United States Patent
Smith et al.

(10) Patent No.: US 10,412,131 B2
(45) Date of Patent: Sep. 10, 2019

(54) SYSTEMS AND METHODS FOR GESTURE-BASED SHARING OF DATA BETWEEN SEPARATE ELECTRONIC DEVICES

(71) Applicant: PerkinElmer Informatics, Inc., Waltham, MA (US)

(72) Inventors: Robin Smith, Boston, MA (US); Sunil Anant Gupta, Reading, MA (US); Michael Stapleton, Lexington, MA (US); Benjamin James Davis, Torrington, CT (US); Amy Annette Hahn, Morrisville, NC (US); Jordan Haneil Shatsoff, Waltham, MA (US); Joshua Benjamin Wakefield, Durham, NC (US); Biying Huang, Apex, NC (US); Shadrack Cgar Frazier, Sr., Durham, NC (US); Brandon William Arther Graham, Guelph (CA); Beau Guy Tremblay, Arlington, MA (US); Sonal Shashikant Kulkarni, Durham, NC (US); Daniel Oberlin, Bedford, MA (US); Julie E. Nelson, Braintree, MA (US)

(73) Assignee: PerkinElmer Informatics, Inc., Waltham, MA (US)

( * ) Notice: Subject to any disclaimer, the term of this patent is extended or adjusted under 35 U.S.C. 154(b) by 421 days.

(21) Appl. No.: 14/173,934

(22) Filed: Feb. 6, 2014

(65) Prior Publication Data

US 2014/0282106 A1 Sep. 18, 2014

Related U.S. Application Data

(60) Provisional application No. 61/780,849, filed on Mar. 13, 2013.

(51) Int. Cl.
*G06F 3/01* (2006.01)
*H04W 4/21* (2018.01)
(Continued)

(52) U.S. Cl.
CPC .......... *H04L 65/403* (2013.01); *G06F 3/017* (2013.01); *G06F 16/176* (2019.01);
(Continued)

(58) Field of Classification Search
None
See application file for complete search history.

(56) References Cited

U.S. PATENT DOCUMENTS

| 4,967,372 A | 10/1990 | Feldman |
| 5,386,507 A | 1/1995 | Teig et al. |

(Continued)

FOREIGN PATENT DOCUMENTS

| EP | 1526471 A1 | 4/2005 |
| EP | 1613009 A1 | 1/2006 |

(Continued)

OTHER PUBLICATIONS

WindowsNetworking, 2011.*

(Continued)

*Primary Examiner* — Jennifer N To
*Assistant Examiner* — Beau D Spratt
(74) *Attorney, Agent, or Firm* — Banner & Witcoff, Ltd.

(57) ABSTRACT

Described herein are various embodiments of systems, methods, and apparatus that allow a user to share data, such as one or more files from within an application with one or more other (not necessarily co-located) computing devices using a gesture-based sharing function. In a particular example, systems, methods, and apparatus described herein may be used to share graphical representations of chemical structures within a chemical structure rendering application (Continued)

between two or more user devices. By offering a user a quick and visually intuitive option for sharing a file with other user(s) without exiting a current application, the systems, methods, and apparatus described herein provide efficient and engaging tools for sharing work product in real time between two or more users.

3 Claims, 17 Drawing Sheets

(51) Int. Cl.
   H04L 29/06        (2006.01)
   H04M 1/725        (2006.01)
   G06F 16/176       (2019.01)
   G16C 20/80        (2019.01)
   G16C 20/90        (2019.01)

(52) U.S. Cl.
   CPC .......... H04M 1/7253 (2013.01); *G16C 20/80* (2019.02); *G16C 20/90* (2019.02); *H04M 2250/22* (2013.01); *H04M 2250/64* (2013.01); *H04W 4/21* (2018.02)

(56) References Cited

U.S. PATENT DOCUMENTS

| | | | |
|---|---|---|---|
| 5,434,971 A | 7/1995 | Lysakowski, Jr. | |
| 6,017,390 A | 1/2000 | Charych et al. | |
| 6,151,643 A * | 11/2000 | Cheng | G06F 8/62 709/200 |
| 6,304,869 B1 | 10/2001 | Moore et al. | |
| 6,434,490 B1 | 8/2002 | Agrafiotis et al. | |
| 7,250,950 B2 | 7/2007 | Smith et al. | |
| 7,613,574 B2 | 11/2009 | Verseput | |
| 7,650,327 B2 | 1/2010 | Remsen et al. | |
| 7,676,499 B2 | 3/2010 | Dorsett, Jr. | |
| 7,707,206 B2 | 4/2010 | Encina et al. | |
| 7,805,437 B1 | 9/2010 | Andersson et al. | |
| 8,099,445 B1 * | 1/2012 | Masinter | G06F 9/445 707/791 |
| 8,433,723 B2 | 4/2013 | Smith et al. | |
| 8,538,983 B2 | 9/2013 | Huang et al. | |
| 8,782,774 B1 * | 7/2014 | Pahl | H04L 9/0825 726/15 |
| 2002/0049548 A1 | 4/2002 | Bunin | |
| 2002/0107359 A1 | 8/2002 | Hogarth et al. | |
| 2002/0161599 A1 | 10/2002 | Faerman et al. | |
| 2003/0194687 A1 | 10/2003 | Clark | |
| 2004/0003000 A1 | 1/2004 | Smith et al. | |
| 2004/0006742 A1 | 1/2004 | Slocombe | |
| 2004/0024493 A1 | 2/2004 | Fagrell et al. | |
| 2004/0068524 A1 * | 4/2004 | Aboulhosn | G06F 17/30206 |
| 2004/0122641 A1 | 6/2004 | Miller et al. | |
| 2004/0236740 A1 | 11/2004 | Cho et al. | |
| 2004/0249791 A1 | 12/2004 | Waters et al. | |
| 2005/0091289 A1 * | 4/2005 | Shappell | G06F 17/30067 |
| 2005/0091672 A1 * | 4/2005 | Debique | G06F 8/20 719/328 |
| 2005/0094205 A1 | 5/2005 | Lo et al. | |
| 2005/0102313 A1 | 5/2005 | Levering et al. | |
| 2005/0123993 A1 | 6/2005 | Brunner et al. | |
| 2005/0131894 A1 | 6/2005 | Vuong | |
| 2005/0177280 A1 | 8/2005 | Almstetter et al. | |
| 2005/0212759 A1 | 9/2005 | Marvit et al. | |
| 2005/0226495 A1 | 10/2005 | Li | |
| 2006/0061595 A1 | 3/2006 | Goede et al. | |
| 2006/0123113 A1 | 6/2006 | Friedman | |
| 2006/0277201 A1 | 12/2006 | Dorsett | |
| 2007/0016853 A1 | 1/2007 | Abagyan et al. | |
| 2007/0146347 A1 | 6/2007 | Rosenberg | |
| 2007/0174765 A1 | 7/2007 | Schleppenbach et al. | |
| 2007/0260583 A1 | 11/2007 | Domine et al. | |
| 2008/0136785 A1 | 6/2008 | Baudisch et al. | |
| 2008/0140616 A1 | 6/2008 | Encina et al. | |
| 2008/0177885 A1 * | 7/2008 | Pierce | H04L 63/083 709/227 |
| 2008/0189293 A1 * | 8/2008 | Strandel | G06Q 10/107 |
| 2008/0195664 A1 * | 8/2008 | Maharajh | G06F 17/30035 |
| 2008/0213663 A1 | 9/2008 | Hu et al. | |
| 2008/0228774 A1 | 9/2008 | Hamilton et al. | |
| 2009/0006411 A1 | 1/2009 | Lele et al. | |
| 2009/0063427 A1 | 3/2009 | Zuta et al. | |
| 2009/0171975 A1 | 7/2009 | McConnell et al. | |
| 2009/0234876 A1 | 9/2009 | Schigel et al. | |
| 2009/0244015 A1 | 10/2009 | Sengupta et al. | |
| 2009/0273571 A1 | 11/2009 | Bowens | |
| 2010/0137027 A1 | 6/2010 | Kim | |
| 2010/0156812 A1 * | 6/2010 | Stallings | G06F 3/04883 345/173 |
| 2010/0257239 A1 * | 10/2010 | Roberts | G06Q 10/10 709/204 |
| 2010/0257457 A1 | 10/2010 | De Goes | |
| 2011/0083111 A1 * | 4/2011 | Forutanpour | G06F 1/1694 715/863 |
| 2011/0163944 A1 | 7/2011 | Bilbrey et al. | |
| 2011/0221656 A1 | 9/2011 | Haddick et al. | |
| 2011/0276589 A1 | 11/2011 | Smith et al. | |
| 2012/0019488 A1 | 1/2012 | McCarthy | |
| 2012/0078853 A1 | 3/2012 | Huang et al. | |
| 2012/0110486 A1 | 5/2012 | Sirpal et al. | |
| 2012/0173622 A1 | 7/2012 | Toledano et al. | |
| 2012/0188147 A1 | 7/2012 | Hosein et al. | |
| 2012/0216153 A1 * | 8/2012 | Sip | G06F 3/033 715/863 |
| 2012/0246228 A1 | 9/2012 | Udezue et al. | |
| 2012/0272163 A1 * | 10/2012 | Stochosky | H04L 67/10 715/753 |
| 2012/0284638 A1 | 11/2012 | Cutler et al. | |
| 2012/0311038 A1 | 12/2012 | Trinh et al. | |
| 2012/0324368 A1 | 12/2012 | Putz et al. | |
| 2013/0044042 A1 | 2/2013 | Olsson et al. | |
| 2013/0061163 A1 | 3/2013 | Clark et al. | |
| 2013/0218878 A1 | 8/2013 | Smith et al. | |
| 2013/0222265 A1 | 8/2013 | Smith et al. | |
| 2014/0071488 A1 * | 3/2014 | Fukuda | G06F 3/1204 358/1.15 |
| 2014/0089329 A1 | 3/2014 | Kozloski et al. | |
| 2014/0143302 A1 * | 5/2014 | Huang | G06F 9/452 709/203 |
| 2014/0181219 A1 * | 6/2014 | Wang | H04L 51/08 709/206 |
| 2014/0267240 A1 | 9/2014 | Smith | |
| 2014/0324960 A1 * | 10/2014 | Pattan | H04N 21/242 709/203 |
| 2014/0337725 A1 | 11/2014 | Smith et al. | |

FOREIGN PATENT DOCUMENTS

| | | |
|---|---|---|
| EP | 2509286 A2 | 10/2012 |
| GB | 2493830 A | 2/2013 |
| WO | WO-2007092842 A2 | 8/2007 |
| WO | WO-2011/041427 A2 | 4/2011 |
| WO | WO-2011140148 A1 | 11/2011 |
| WO | WO-2012/068548 A1 | 5/2012 |
| WO | WO-2013126077 A1 | 8/2013 |

OTHER PUBLICATIONS

Microsoft Lync How to Guie, 2012.*
International Search Report for PCT/US2014/015131, dated Aug. 21, 2014, 6 pages.
Written Opinion for PCT/US2014/015131, dated Aug. 21, 2014, 10 pages.
Carmingniani, J. et al., Augmented Reality Technologies, Systems and Applications, Multimedia Tools and Applications 51:341-377, (2011).
Clark A. M., Basic Primitives for Molecular Diagram Sketching, Journal of Cheminformatics 2:8 (2010).
European Search Report for 13275308.8, dated Apr. 9, 2014, 4 pages.

(56) References Cited

OTHER PUBLICATIONS

European Search Report for 13275308.8, dated Aug. 13, 2014, 8 pages.
Furlon, Rod, Build Your Own Google Glass, Resources Hands On, IEEE Spectrum, IEEE Inc., vol. 50, No. 1, pp. 20-21, (Jan. 1, 2013).
Giudice N. A. et al., Learning Non-Visual Graphical Information Using a Touch-Based Vibro-Audio Interface, Proceedings of the 14th International ACM Sigaccess Conference on Computers and Accessibility, Assets '12, 103-110 (Jan. 1, 2012).
International Search Report for PCT/US2014/016249, dated Aug. 13, 2014, 4 pages.
International Search Report for PCT/US2014/035685, dated Aug. 4, 2014, 4 pages.
Li et al., Personal Experience with Four Kinds of Chemical Structure Drawing Software: Review on ChemDraw, ChemWindow, ISIS/Draw, and ChemSketch, J. Chem. Inf. Comput. Sci. 44:1886-1890 (2004).
Toennies J. L. et al., Toward Haptic/Aural Touchscreen Display of Graphical Mathematics for the Education of Blind Students, WHC, IEEE, 373:378 (2011).
Written Opinion for PCT/US2014/016249, dated Aug. 13, 2014, 7 pages.
Written Opinion for PCT/US2014/035685, dated Aug. 4, 2014, 8 pages.
Algorri et al., Reconstruction of Chemical Molecules from Images, 2007 Annual International Conference of the IEEE Engineering in Medicine and Biology Society (EMBC '07), Lyon, France, Aug. 22-26, 2007, in Conjunction with the Biennial Conference of the Societe Francaise de Genie Biologique et Medical (SFGB), Aug. 22, 2007, pp. 4609-4612.
Australian Patent Application No. 2011248243, APO Examination Report No. 1, dated Nov. 5, 2013, 3 pages.
Bennett, Samsung's AllShare Play pushes pictures from phone to cloud and TV, <http://news.cnet.com/8301-1035_3-57391735-94/samsungs-allshare-play-pushes-pictures-from-phone-to-cloud-and-tv/> [retrieved Oct. 24, 2013], Mar. 6, 2012, 9 pages.
Casey et al., Optical Recognition of Chemical Graphics, Document Analysis and Recognition, 1993, Proceedings of the Second International Conference on, Tsukuba Science City, Japan, Oct. 20-22, 1993, Los Alamitos, CA, USA, IEEE Comput. Soc., Oct. 20, 1993, pp. 627-631.
Filippov et al., Optical Structure Recognition Software to Recover Chemical Information: OSRA, An Open Source Solution, Journal of Chemical Information and Modeling, vol. 49, No. 3, Mar. 23, 2009, pp. 740-743.
First Office Action, Chinese Application No. 201190000597.X, dated May 29, 2013, 4 pages Including Translation.
Flick—Simply the easiest way to share, <http://getflick.io/> [retrieved Aug. 23, 2013], 4 pages.
Gonzalez-Villanueva et al., WallShare: A Collaborative Multi-pointer System for Portable Devices, Nov. 19, 2012, 7 pages.
International Search Report, PCT/US2011/035070, dated Oct. 6, 2011, 4 pages.
International Search Report, PCT/US2011/061534, dated Mar. 16, 2012, 2 pages.
International Search Report, PCT/US2012/026574, dated Mar. 20, 2013, 4 pgs.
iTunes Preview, Flick for iPhone, iPad, and iPod touch on the iTunes App Store, <https://itunes.apple.com/us/app/flick/id644265534?mt=8> [retrieved Oct. 28, 2013], 2 pages.
Jurach T., Microsoft Outlook Quick Start Email Guide!, 1-3 (2006).
Kim et al., Development of a Gesture-Based Molecular Visualization Tool Based on Virtual Reality for Molecular Docking, Bull. Korean Chem. Soc. 2004, vol. 25, No. 10 pp. 1571-1574.
Layar, What is Layar?, <http://www.layar.com/features/> [retrieved Nov. 14, 2012], 7 pages.
Lorensen et al., Marching Cubes: A high resolution 3D surface construction algorithm. In: Computer Graphics, vol. 21, Nr. 4, Jul. 1987.
Lucero et al., Pass-Them-Around: Collaborative Use of Mobile Phones for Photo Sharing, CHI 2011—Session: Photo Sharing, May 7-11, 2011, Vancouver, BC, Canada, 10 pages.
Park et al., Automated Extraction of Chemical Structure Information From Digital Raster Images, Chemistry Central Journal, Biomed Central Ltd., vol. 3, No. 1, Feb. 5, 2009, pp. 1-16.
Park et al., Tunable Machine Vision-Based Strategy for Automated Annotation of Chemical Databases, Journal of Chemical Information and Modeling, vol. 49, No. 8, 2009, pp. 1993-2001.
Pering et al., Enabling Pervasive Collaboration with Platform Composition, Intel Research Santa Clara, 2009, 18 pages.
Pering et al., Spontaneous Marriages of Mobile Devices and Interactive Spaces, Communications of the ACM, Sep. 2005, vol. 48, No. 9, pp. 53-59, 7 pages.
Scheible et al., MobiToss: A Novel gesture based interface for creating and sharing mobile multimedia art on large public displays, MM'08, Oct. 26-31, 2008 Vancouver British Columbia, Canada, pp. 957-960, 4 pages.
Shine et al., ChemPad3 a tutorial, May 21, 2008, 10 pages.
TSOTSIS, Word Lens Translates Words Inside of Images. Yes Really., <http://techcrunch.com/2010/12/16/world-lens-translates-words-inside-of-images-yes-really/> [retrieved Nov. 14, 2012], Dec. 16, 2010, 3 pages.
Valko et al., CLiDE Pro: The Latest Generation of CLiDE, a Tool for Optical Chemical Structure Recognition, Journal of Chemical Information and Modeling, vol. 94, No. 4, 27 Apr. 2009, pp. 780-787.
Weinberg et al., ZooZBeat: a Gesture-based Mobile Music Studio, NIME 2009, pp. 312-315, 4 pages.
Williams et al., Smart Phones, a Powerful Tool in the Chemistry Classroom, Journal of Chemical Education, 2011, pp. 683-686.
Williams et al., Mobile apps for chemistry in the world of drug discovery, Drug Discovery Today, vol. 16. Nos. 21/22, Nov. 2011, pp. 928-939.
Wobbrock et al., User-Defined Gestures for Surface Computing, CHI—Tabletop Gestures, Apr. 7, 2009, pp. 1083-1092.
Written Opinion, PCT/US2011/035070, dated Oct. 6, 2011, 9 pages.
Written Opinion, PCT/US2011/061534, dated Mar. 16, 2012, 5 pages.
Written Opinion, PCT/US2012/026574, dated Mar. 20, 2013, 8 pgs.
Jun. 7, 2019—(EP) Communication pursuant to Rule 164(2)(b) and Article 94(3)—App 14708158.2.

\* cited by examiner

SYSTEMS AND METHODS FOR GESTURE-BASED SHARING OF DATA BETWEEN SEPARATE ELECTRONIC DEVICES

RELATED APPLICATIONS

The present application claims the benefit of and priority to U.S. Provisional Application Ser. No. 61/780,849 entitled "Systems and Methods for Gesture-Based Sharing of Data Between Separate Electronic Devices" filed Mar. 13, 2013, the contents of which is hereby incorporated by reference in its entirety.

BACKGROUND

Chemical structure rendering software is widely used by research and educational institutions to depict chemical structures and chemical reactions of interest. Unlike chemical formulas or chemical names, structural formulas provide a graphical representation of the molecular structure. A graphical chemical structure representation is capable of indicating the arrangements of atoms in a way that a chemical formula cannot.

Many techniques are available for file sharing and workspace collaboration, including shared desktop views, cloud collaboration solutions, Bump™ by Bump Technologies of Mountain View, Calif. for physically transferring files upon physically bumping two mobile devices together, peer-to-peer file sharing (P2P) protocol for sharing files between member devices of a file sharing system, and direct connect protocol for transferring files from one computing device to another over a central hub.

There is a need for a file sharing and collaboration tool that is not application-dependent (e.g., does not require all member computing devices to view/modify/share the file(s) using the same software application) and not location-dependent (e.g., computing devices are not necessarily co-located during file sharing and collaboration).

SUMMARY OF ILLUSTRATIVE EMBODIMENTS

Described herein are various embodiments of systems, methods, and apparatus that allow a user to share data, such as one or more files from within an application with one or more other (not necessarily co-located) computing devices using a gesture-based sharing function. In a particular example, systems, methods, and apparatus described herein may be used to share graphical representations of chemical structures within a chemical structure rendering application between two or more user devices. By offering a user a quick and visually intuitive option for sharing a file with other user(s) without exiting a current application, the systems, methods, and apparatus described herein provide efficient and engaging tools for sharing work product in real time between two or more users.

In various embodiments, the systems, methods, and apparatus utilize or include a tablet computer, a mobile phone device, or any other computer device or system capable of receiving gesture-based input. The systems, methods, and apparatus have applications in a wide variety of environments and/or industries that involve collaborative review and/or editing by users who are not necessarily co-located. For example, the systems, methods, and apparatus have applications in a wide variety of industries that create and edit structural formulas, such as the reagent industry, the publishing industry, and/or the web search industry.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

In one aspect, the invention is directed to a method comprising: receiving, via a user interface, selection of at least one file for sharing with a separate computing device; identifying, by a processor of a computing device, one or more members for sharing; causing, by the processor, presentation of one or more graphical identifiers within a display area of the computing device, wherein each graphical identifier of the one or more graphical identifiers is representative of a respective member of the one or more members, wherein the one or more graphical identifiers represent at least a portion of the one or more members; identifying, by the processor, a user input gesture indicative of moving the at least one file towards at least a first graphical identifier of the one or more graphical identifiers; responsive to identifying the user input gesture, causing, by the processor, presentation of a graphical representation of the at least one file moving towards the at least the first graphical identifier, and issuing, by the processor, via a network, a request for data sharing, wherein the request for data sharing comprises a member identifier associated with the first graphical identifier, and the request for data sharing comprises information associated with the at least one file; and receiving, via the network, responsive to the request for data sharing, an acknowledgment of data sharing, wherein the acknowledgment comprises the member identifier.

In some embodiments, the gesture is a "flick" or "fling" gesture (e.g., a sweeping gesture) made, for example, with a finger (or fingers), hand, head, or other body part(s) of the user. In some embodiments, the gesture indicative of moving the at least one file towards at least a first graphical identifier is distinguished from a "drag and drop" gesture in that the at least one file continues to move toward the first graphical identifier after completion of the gesture by the user and/or after the end of contact between the user and the (a) touchscreen or display screen (e.g., the file continues to move in the direction of the gesture after the user's finger(s) lifts off the surface of the touchscreen). In some embodiments, the graphical identifiers are sufficiently far apart to prevent inadvertent transmission of a file to an unintended recipient.

In some embodiments, receiving selection of the at least one file comprises identifying a user input gesture indicative of selection of the at least one file. In some embodiments, identifying one or more members for sharing comprises: issuing, via the network, an availability request; and responsive to the availability request, receiving indication of one or more member identifiers, wherein each member identifier of the one or more member identifiers is associated with a respective computing device executing a sharing application in communication with the network.

In some embodiments, causing presentation of the one or more graphical identifiers comprises, for each graphical identifier of the one or more graphical identifiers, causing presentation of at least one of a name, an icon, and an image associated with the respective member represented by the respective graphical identifier. In some embodiments, the one or more graphical identifiers are arranged radially surrounding a graphical representation of the at least one file. In some embodiments, causing presentation of the one or more graphical identifiers comprises identifying the portion of the one or more members based at least in part on one or more of a frequency and a recency of file sharing with the computing device. In some embodiments, causing presentation of the one or more graphical identifiers comprises identifying the portion of the one or more members based at least in part on a determination of co-location of the computing device with respective computing devices of at least one of the portion of the one or more members. In some embodiments, co-location is determined based in part upon near field communications. In some embodiments, causing presentation of the one or more graphical identifiers comprises identifying selection of a particular group of users.

In some embodiments, at least one of the one or more members comprises a device selected from the group consisting of a printer, a television, a smart TV, a projector, a media player, and a facsimile.

In some embodiments, the at least one file is selected within a software application; and the method is performed by a sub-application configured to execute within the software application. In some embodiments, the sub-application is configured to execute within two or more software applications installed upon the computing device.

In some embodiments, identifying the user input gesture comprises identifying a sweeping gesture across a touch screen.

In some embodiments, the graphical representation of the at least one file moving towards at least the first graphical identifier comprises a spinning animation. In some embodiments, the graphical representation of the at least one file moving towards at least the first graphical identifier comprises a gradual size reduction.

In some embodiments, the information associated with the at least one file comprises an identification of a network file location. In some embodiments, the method further comprises, responsive to receiving the acknowledgment, causing presentation, within the display area, of a notification indicative of success of sharing. In some embodiments, the method further comprises, after receiving the acknowledgement: receiving, via the network, an alert regarding data availability, wherein the alert is associated with a modified version of a first file of the at least one file; issuing, by the processor via the network, responsive to the alert, a request for the modified version of the first file; receiving, via the network, the modified version of the first file, wherein the first file has been modified by a first member of the one or more members; and causing presentation of the modified version of the first file within the display area. In some embodiments, causing presentation of the modified version of the first file comprises causing presentation of an indication of the first member. In some embodiments, the alert comprises a session identifier; and the request for the modified version of the first file comprises the session identifier.

In another aspect, the invention is directed to a method comprising: receiving, via a network from a first data share application installed on a first user computing device, a request for data share, wherein the request comprises at least one file and at least one target user; determining, by a processor of a computing device, an identification of a second user computing device, wherein the second user computing device is associated with a first target user of the at least one target user; issuing, by the processor, via the network, an alert to the target user regarding data availability, wherein the alert is issued through a second sharing application installed on a second user computing device; responsive to the alert, receiving, from the second user computing device, a request for available data; and responsive to the request for available data, retrieving, by the processor, the at least one file, and providing, via the network, the at least one file, wherein the at least one file is provided to the second sharing application.

In some embodiments, the method further comprises, prior to receiving the request for data share: receiving, via the network from the first data share application, a request to identify members available for sharing; and identifying, by the processor, one or more members available for sharing, wherein each member of the one or more members are associated with a user of the first user computing device. In some embodiments, the sharing application comprises a sub-application in communication with a software application; and identifying the one or more members for sharing comprises identifying respective ability of each computing device associated with the one or more member identifiers to view a file type associated with the software application.

In another aspect, the invention is directed to a system comprising: a processor; and a memory having instructions stored thereon, wherein the instructions, when executed by the processor, cause the processor to: receive, via a user interface, selection of at least one file for sharing with a separate computing device; identify one or more members for sharing; cause presentation of one or more graphical identifiers within a display area of the computing device, wherein each graphical identifier of the one or more graphical identifiers is representative of a respective member of the one or more members, wherein the one or more graphical identifiers represent at least a portion of the one or more members; identify a user input gesture indicative of moving the at least one file towards at least a first graphical identifier of the one or more graphical identifiers; responsive to identifying the user input gesture, cause presentation of a graphical representation of the at least one file moving towards the at least the first graphical identifier, and issue, via a network, a request for data sharing, wherein the request for data sharing comprises a member identifier associated with the first graphical identifier, and the request for data sharing comprises information associated with the at least one file; and receive, via the network, responsive to the request for data sharing, an acknowledgment of data sharing, wherein the acknowledgment comprises the member identifier.

In some embodiments, the gesture is a "flick" or "fling" gesture (e.g., a sweeping gesture) made, for example, with a finger (or fingers), hand, head, or other body part(s) of the user. In some embodiments, the gesture indicative of moving the at least one file towards at least a first graphical identifier is distinguished from a "drag and drop" gesture in that the at least one file continues to move toward the first graphical identifier after completion of the gesture by the user and/or after the end of contact between the user and the (a) touchscreen or display screen (e.g., the file continues to move in the direction of the gesture after the user's finger(s) lifts off the surface of the touchscreen). In some embodiments, the graphical identifiers are sufficiently far apart to prevent inadvertent transmission of a file to an unintended recipient.

In another aspect, the invention is directed to a non-transitory computer readable medium having instructions stored thereon, wherein the instructions, when executed by a processor, cause the processor to: receive, via a user interface, selection of at least one file for sharing with a separate computing device; identify one or more members for sharing; cause presentation of one or more graphical identifiers within a display area of the computing device, wherein each graphical identifier of the one or more graphical identifiers is representative of a respective member of the one or more members, wherein the one or more graphical identifiers represent at least a portion of the one or more members; identify a user input gesture indicative of moving the at least one file towards at least a first graphical identifier of the one or more graphical identifiers; responsive to identifying the user input gesture, cause presentation of a graphical representation of the at least one file moving towards the at least the first graphical identifier, and issue, via a network, a request for data sharing, wherein the request for data sharing comprises a member identifier associated with the first graphical identifier, and the request for data sharing comprises information associated with the at least one file; and receive, via the network, responsive to the request for data sharing, an acknowledgment of data sharing, wherein the acknowledgment comprises the member identifier. In some embodiments, the gesture is a "flick" or "fling" gesture (e.g., a sweeping gesture) made, for example, with a finger (or fingers), hand, head, or other body part(s) of the user. In some embodiments, the gesture indicative of moving the at least one file towards at least a first graphical identifier is distinguished from a "drag and drop" gesture in that the at least one file continues to move toward the first graphical identifier after completion of the gesture by the user and/or after the end of contact between the user and the (a) touchscreen or display screen (e.g., the file continues to move in the direction of the gesture after the user's finger(s) lifts off the surface of the touchscreen). In some embodiments, the graphical identifiers are sufficiently far apart to prevent inadvertent transmission of a file to an unintended recipient.

In another aspect, the invention is directed to a system comprising: a processor; and a memory having instructions stored thereon, wherein the instructions, when executed by the processor, cause the processor to: receive, via a network from a first data share application installed on a first user computing device, a request for data share, wherein the request comprises at least one file and at least one target user; determine an identification of a second user computing device, wherein the second user computing device is associated with a first target user of the at least one target user; issue, via the network, an alert to the target user regarding data availability, wherein the alert is issued through a second sharing application installed on a second user computing device; responsive to the alert, receive, from the second user computing device, a request for available data; and responsive to the request for available data, retrieve the at least one file, and provide, via the network, the at least one file, wherein the at least one file is provided to the second sharing application.

In another aspect, the invention is directed to a non-transitory computer readable medium having instructions stored thereon, wherein the instructions, when executed by a processor, cause the processor to: receive, via a network from a first data share application installed on a first user computing device, a request for data share, wherein the request comprises at least one file and at least one target user; determine an identification of a second user computing device, wherein the second user computing device is associated with a first target user of the at least one target user; issue, via the network, an alert to the target user regarding data availability, wherein the alert is issued through a second sharing application installed on a second user computing device; responsive to the alert, receive, from the second user computing device, a request for available data; and responsive to the request for available data, retrieve the at least one file, and provide, via the network, the at least one file, wherein the at least one file is provided to the second sharing application.

BRIEF DESCRIPTION OF THE DRAWINGS

The foregoing and other objects, aspects, features, and advantages of the invention will become more apparent and may be better understood by referring to the following description taken in conjunction with the accompanying drawings, in which.

Figure 1:
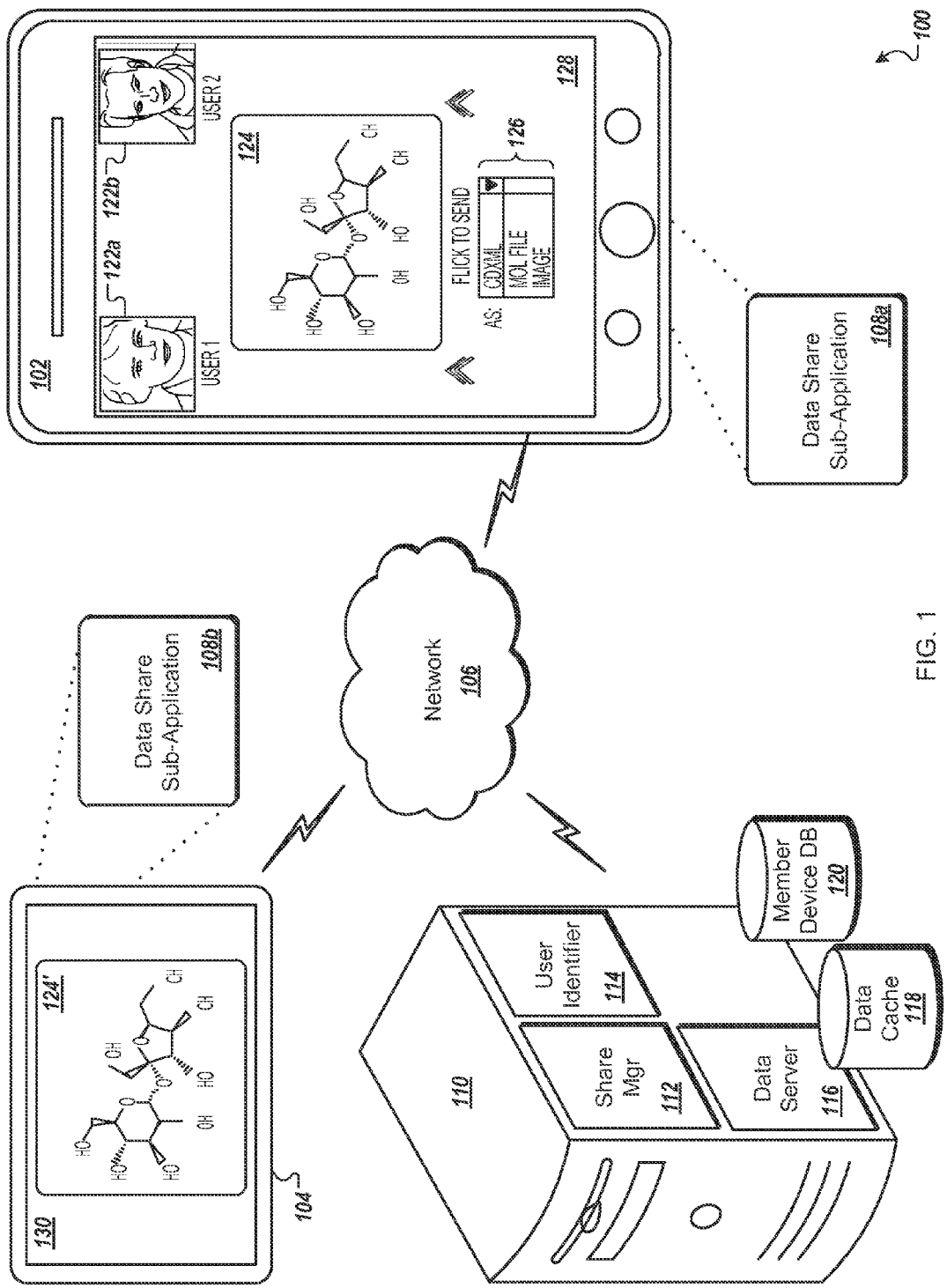
FIG. 1 is an example system for gesture-based sharing of data between computing devices.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DESCRIPTION

It is contemplated that apparatus, systems, and methods of the claimed invention encompass variations and adaptations developed using information from the embodiments described herein. Adaptation and/or modification of the apparatus, systems, and methods described herein may be performed by those of ordinary skill in the relevant art.

Throughout the description, where apparatus and systems are described as having, including, or comprising specific components, or where processes and methods are described as having, including, or comprising specific steps, it is contemplated that, additionally, there are apparatus and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

In general, in various embodiments, the present invention pertains to apparatus, systems, and methods for gesture-based sharing of data between separate computing devices. The computing device may be, for example, a personal computer, a workstation, a tablet computer (e.g., an Apple®

IPad® by Apple Inc. of Cupertino, Calif.), computerized eye glasses, or a mobile phone device. As used herein, the term "molecular scaffold" refers to a portion (e.g., a fragment) of a graphical representation of a chemical structure.

Referring to FIG. 1, an example system 100 for gesture-based sharing of data between separate computing devices includes a first computing device 102 sharing information (e.g., a graphical rendering of a chemical structure 124) with a second computing device 104 over a network 106 via data share sub-applications 108 configured to communicate with a server 110 providing a network-based sharing service. Users of the first computing device 102 and the second computing device 104, for example, may be registered as members of the network-based sharing service (e.g., member information may be stored in a member device database 120 included in and/or in communication with the server 110).

In operation, a user of the first computing device 102 may identify the chemical structure 124 for sharing with one or more members of the network-based sharing service. For example, the user may select a share function (not illustrated) to open the data share sub-application 108a functionality within a presently executing application. The data share sub-application 108a, in some implementations, is configured to execute as an overlay to one or more applications installed upon the computing device 102. The applications, for example, are configured for creation, editing, and/or manipulation of data files such as, in some examples, word processing software, presentation software, spreadsheet software, program development software, graphic editing software, graphical chemical structure software, graphical biological structure software, photo manipulation software, and video manipulation software.

The data share sub-application 108a, executing upon the first computing device 102 (e.g., a mobile computing device such as a smart phone or computerized eye glasses), may identify one or more members 122 eligible for sharing the chemical structure 124. The members may be identified, in some examples, based upon one or more of a recency of sharing with the computing device 102 (e.g., same day, same week, same month, etc.), a frequency of sharing with the computing device 102, a total number of shares between the computing device 102 and a computing device associated with the respective member, an indication by the user of the computing device 102 designating the respective member as a favorite, a status of the respective member (e.g., identified by a user identifier feature 114 of the server 110 as being "online," "active," or otherwise available for sharing), and an indication from the user of the computing device 102 designating a particular group for sharing (e.g., engineering team, managerial team, immediate family, relatives, social club, etc.). In another example, one or more eligible members may be identified based in part upon a proximity of a computing device associated with the respective user and the computing device 102 (e.g., same room, same building, etc.). For example, the data share sub-application 108a, through a peripheral communication feature of the computing device 102 (e.g., Bluetooth®, Wi-Fi™, NFC, etc.), may attempt to locate one or more member computing devices within range. In this manner, a user of the computing device 102 may identify team members within a conference room for sharing and collaboration. In some implementations, eligible members can include non-user computing devices such as, in some examples, a printer, a facsimile, a television, a smart TV, a projector, or a media player. For example, the data share sub-application 108a may identify, via a peripheral communication feature, nearby computing equipment configured to share files via the data share sub-application 108.

Out of the identified members, the data share sub-application 108a, in some implementations, identifies a subset of the members 122 for presentation within a display area 128 of the computing device 102. For example, the data share sub-application 108a may identify members 122 to display radially surrounding the chemical structure 124. For example, the data share sub-application 108a may identify up to four members 122 to display within the four corners of the display area 128 and/or up to four members (not illustrated) to display along the four edges of the display area 128 (e.g., as illustrated in a screen shot 420 of FIG. 4B). In another example (not illustrated), the data share sub-application 108a may arrange two or more members along a single edge of the display area 128 as illustrated in relation to FIG. 5.

In some implementations, the user is presented with two or more file format options for sharing data such as the chemical structure 124. For example, as illustrated within the display area 128, the user of the computing device 102 can choose to share the chemical structure 124 as a variety of file types 126 such as a CDXML file, a MOL file, or an image file. The chemical structure 124, for example, may be loaded presently as a CDXML file. Selection of a different file type 126, in some implementations, causes conversion of the chemical structure 124 into a different file type prior to sharing. The data share sub-application 108a, for example, may call into a "save as" function of the presently executing software application (e.g., a chemical structure drawing and manipulation program) to modify the file type of the chemical structure 124 prior to sharing with one or both of the users 122.

In some implementations, the data share sub-application 108a determines a file type for sharing based in part upon the capabilities of member computing devices, such as the computing device 104. For example, if the computing device 104 has an image file presentation application installed, but not a chemical structure drawing and manipulation program, the data share sub-application 108a may identify that the chemical structure 124 should be converted to an image file prior to sharing with the second computing device 104. The data share sub-application 108b, executing upon the second computing device 104, in some implementations, indicates to the server 110 a list of eligible file types (e.g., file types renderable by one or more applications interfacing with the data share sub-application 108b). The server 110, in turn, may provide this information to the first computing device 102, for example, upon presentation of the members 122.

In some implementations, to share a file with one of the members 122, the user of the first computing device 102 "pushes" the chemical structure 124 towards one or both of the graphical representations of the members 122. For example, the user may "flick" or "fling" the image of the chemical structure 124 towards the upper right corner of the display 128 with a sweeping gesture across a touch screen display to share the chemical structure 124 with user 2 122b. In another example, the user may "flick" or "fling" the image of the chemical structure 124 towards the upper left hand corner of the display 128 with a sweeping head or hand gesture made using a computerized eye glasses to share the chemical structure 124 with user 122a. In another example, the user may "flick" or "fling" the image of the chemical structure 124 towards the upper left hand corner of the display 128 with a sweeping gesture made using a stylus to share the chemical structure 124 with user 122a.

Upon performing the sweeping gesture, in some implementations, the data share sub-application 108a illustrates the chemical structure 124 as moving across the display 128 towards the intended member(s) 122. For example, the chemical structure 124 may be illustrated as floating or flying towards the intended member(s) 122. In some implementations, the chemical structure 124 may be animated as spinning, flipping, morphing, and/or shrinking while moving towards the intended member(s) 122.

Upon performing the sweeping gesture, in some implementations, the data share sub-application 108a provides a member identifier associated with the intended member(s) 122 and an indication of the chemical structure 124 (e.g., a file, a network file location, etc.) to a share manager 112 of the server 110. The user identifier 114 of the server 110, for example, may identify account information (e.g., computing device identifier, user name, IP address, etc.) of the provided member identifier. Upon successfully matching the member identifier to account information stored in the member device database 120, for example, the share manager 112 may proceed to share the chemical structure 124 with the data share sub-application 108b of the second computing device 104.

The share manager 112, in some implementations, issues an alert to the second computing device 104 regarding availability of the shared chemical structure 124 to the data share sub-application 108b of the second computing device 104. The alert, in some examples, may include a file name, brief file description, identification of the sharing member (e.g., the user of the first computing device 102), a file type, and/or a recommended software application for viewing the chemical structure 124 (e.g., so that the user of the first computing device 102 and the user of the second computing device 104 are reviewing the file within the same software application, if possible).

In some implementations, a data server 116 of the server 110 stores a copy of the chemical structure 124 in a data cache 118 along with a session identifier associated with the offer to share. The share manager 112, for example, may issue the session identifier in the alert to the data share sub-application 108b.

Upon sharing the chemical structure 124 with the user of the second computing device 104, in some implementations, the data share sub-application 108a presents a notification within the display area 128 of the first computing device 102, alerting the user to the sharing of the chemical structure 124. The notification, in some examples, may include one or more of an indication of status (e.g., acceptance or rejection of the offer to share, success or failure in file transfer, etc.), an intended member (e.g., user 1 122a, etc.), a file name, a time stamp, and information regarding the user of the second computing device 104. In a particular example, the notification may identify a user name of the user of the second computing device and an indication of status, as illustrated in the notification message 332 within a screenshot 330 of FIG. 3C.

Similarly, upon receipt of the alert, the data share sub-application 108b, in some implementations, presents a notification within a display region 130 of the second computing device 104. The notification, for example, may provide the second user with the option to review the shared file (e.g., download from the server 110 and open within a software application configured to present the indicated file type). The notification, in some examples, may include one or more of a file name, a file type, information regarding the user of the first computing device 102, a file size, and a timestamp of the notification. In a particular example, the notification may identify a user name of the user of the first computing device, a file type, and a time of share, as illustrated in a notification message 342 in a screenshot 340 of FIG. 3D. In a second example, the notification may identify the user name of the user of the first computing device, the file type, and options to download or decline the offer to share, as illustrated in a notification message 352 within a screenshot 350 of FIG. 3E.

In some implementations, upon acceptance of the offer to share (e.g., positive response to the presented notification) by the user of the second computing device 104, the data share sub-application 108b retrieves the shared file of the chemical structure 124 from the data server 116 (e.g., retrieved from the data cache 118). The data share sub-application 108b, in some implementations, causes presentation of a shared version of the chemical structure 124' within the display area 130 of the second computing device 104.

The users of the first computing device 102 and the second computing device 104, in this manner, may continue to develop the chemical structure 124 by sharing, modifying, and sharing again. In some implementations, features provided by the data share sub-application 108 may allow the users of the computing devices 102, 104 to communicate directly about the shared file, for example using text, voice, and/or video communication.

Further examples of user interfaces and features of the data share sub-application and corresponding network-based sharing service are described below.

Figure 2:
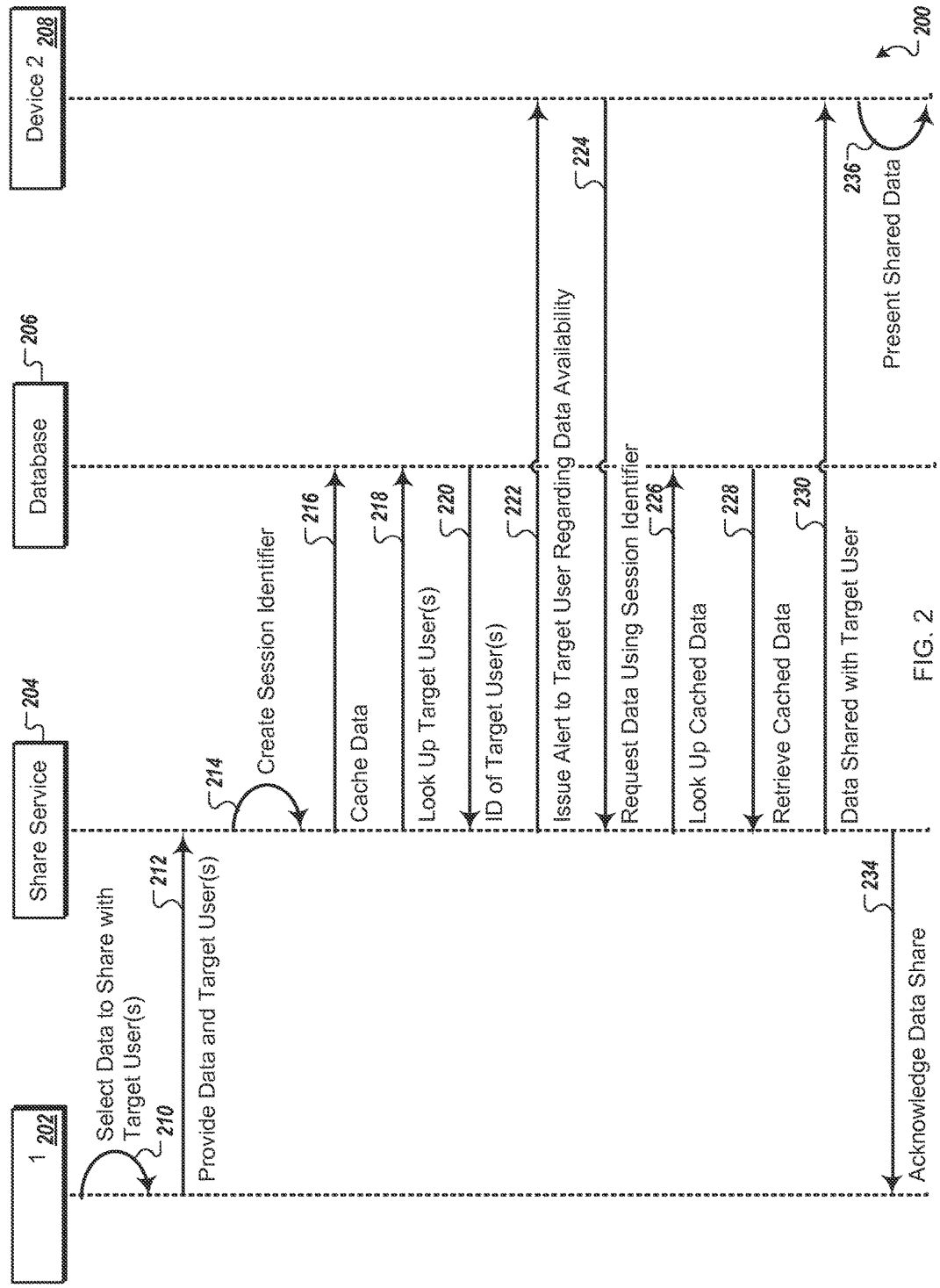
FIG. 2 is a flow diagram of an example method for gesture-based sharing of data between computing devices.

FIG. 2 is a flow diagram of an example method 200 for gesture-based sharing of data between a first computing device 202 and a second computing device 208 via a network-based sharing service 204. The method 200, for example, may be performed by the system 100 for gesture-based sharing of data between separate computing devices as described in relation to FIG. 1.

In some implementations, the method 200 begins with selecting, upon the first computing device 202, data to share with one or more target users (210). The data may include one or more files, such as the chemical structure 124 described in relation to FIG. 1. The data may be selected, for example, by opening a data sharing dialogue within a software application. The data sharing dialogue, for example, may be provided by the data share sub-application 108a of FIG. 1 (e.g., as a sub-application feature layer on top of a presently executing software application). The underlying software application, for example, may be configured for creation, editing, and/or manipulation of data files such as, in some examples, word processing software, presentation software, spreadsheet software, program development software, graphic editing software, graphical chemical structure software, graphical biological structure software, photo manipulation software, and video manipulation software. A sharing session may be opened, in a particular example, through selecting a sharing option 306 within a display region 304 of a computing device 302, as illustrated in a screen shot 300 of FIG. 3A. During setup of a sharing session, in a particular example, a user may select multiple files 406 (e.g., file 406c, file 406e, and file 406l) to share with one or more members by sending the multiple files to a Launchpad region 442, as illustrated in a screen shot 440 of FIG. 4D.

Returning to FIG. 2, during a sharing session, in some implementations, the user is presented with two or more file format options for sharing data such as the chemical structure 124 as illustrated in FIG. 1. The data share sub-application of the first computing device 202 may determine a file type for sharing based in part upon the capabilities of member computing devices, such as the computing device 208. For example, if the computing device 208 has an image file presentation application installed, but not a chemical structure drawing and manipulation program, the data share sub-application of the second computing device 208 may identify that the data, such as a chemical structure, should be converted to an image file prior to sharing with the second computing device 208. The data share sub-application of the second computing device 208, in some implementations, indicates to the share service 204 a list of eligible file types (e.g., file types renderable by one or more applications interfacing with the data share sub-application of the second computing device 208). The share service 204, in turn, may provide this information to the first computing device 202, for example, upon presentation of the users from whom the user of the first computing device may select to share the data.

In some implementations, one or more target users are identified along with the data (210). In some implementations, target users are identified when the user of the first computing device 202 "pushes" the data to be shared towards one or more graphical representations of target users, as illustrated in FIG. 1. For example, the user may "flick" or "fling" the data to be shared (e.g., touch gesture on a touch screen, stylus gesture, sweeping gesture made with a wearable computing device such as computerized glasses, etc.) towards one or more graphical representations of users with whom the user wishes to share the data. In another example, the user may pull back and release on a graphical representation of the data like releasing a sling shot. In a particular example, the user may "flick" or "fling" an image of a chemical structure 308 towards the upper left hand corner of the display region (e.g., with a general movement from point 324a to point 324b) to share the chemical structure 308 with user Alan 328a, as illustrated in a screen shot 320 of FIG. 3B. In a more general sense, a user of a computing device 302 may "push" the chemical structure 324 in the direction of any member to share the chemical structure 324 with the member. Upon performing the sweeping gesture, in some implementations, the data share sub-application illustrates the data as moving across the display of the first computing device towards the graphical representations of member(s) intended as recipients of the data. For example, the data may be illustrated as floating or flying towards the intended user(s). In some implementations, the data may be animated as spinning, flipping, morphing, and/or shrinking while moving towards the intended user(s). In some implementations, an audible indication is provided during sharing. For example, an "in motion" noise may be followed by an "impact" noise to indicate that the flung data has "hit" a target (e.g., graphical representation of a member). In some implementations, a visual indication may be displayed upon sharing data with a target member via a sweeping gesture. For example, the graphical indicator representing the target member may enlarge, change color, light up, and/or animate (e.g., spin, flip, tilt back & forth, etc.) to indicate that the data has been shared with (and/or offered to via the sharing service) the target member.

Returning to FIG. 2, in some implementations, data and target user(s) are provided (212) to the share service 204. Upon performing the sweeping gesture, in some implementations, the data share sub-application of the first computing device 202 provides a user identifier associated with the target user(s) and an indication of the data (e.g., a file, a network file location of the data, etc.) to the share service 204. In some implementations, the share service 204 creates a session identifier associated with the targeted user(s) and an indication of the data (214). In some implementations, the communication between the first computing device 202 and the share service 204 is via HTTP communication. The share service 204 may include one or more servers. The server(s) may be JAVA™-based servers.

In some implementations, the share service 204 caches the data (216) in a database 206. The share service 204, in some implementations, caches a copy of the data along with the account information, including the session identifier associated with the offer to share in the database 206. The database 206, for example, can include one or more of the data cache 118 and the member device database 120, described in relation to FIG. 1.

In some implementations, the share service 204 looks up the target users (218) in the database 206. In some implementations, the database 206 returns the identification of the target user(s) (220) in response to the lookup request.

The share service 204, in some implementations, issues an alert (222) regarding availability of the data to the data share sub-application of the second computing device 208. The alert, in some examples, may include a file name, brief file description, identification of the sharing member (e.g., the user of the first computing device 202), a file type, and/or a recommended software application for viewing the data (e.g., so that the user of the first computing device 202 and the user of the second computing device 208 are reviewing the file within the same software application, if possible). The alert, in some implementations, is issued to the target users based on the identification information obtained in step 220. In some implementations, the alert is communicated to a push notification service provider. The communication between the server(s) of the share service 204 and the push notification service provider may be HTTP communications. The push notification service provider, in some implementations, communicates with a push notification management system. The push notification management system may be specific to the computing device. In some implementations, the push notification management system communicates with the computing device to provide push notifications. The push notification management system, in some implementations, communicates via Raw TCP with the computing device to provide push notifications. In some implementations, the push notification system communicates with the second computing device 208 to issue the alert to the target user regarding the availability of the data the user of the first computing device 202 has shared.

Upon receipt of the alert, the data share sub-application associated with the second computing device 208, in some implementations, presents a notification within a display region of the second computing device. The notification, for example, may provide the second user with the option to review the shared file (e.g., download via the share service 204 and open within a software application configured to present the indicated file type). The notification, in some examples, may include one or more of a file name, a file type, information regarding the user of the first computing device, a file size, and a timestamp of the notification. In a particular example, the notification may identify a user name of the user of the first computing device, a file type, and a time of share, as illustrated in a notification message 342 in a screenshot 340 of a computing device 344, as illustrated in FIG. 3D. In a second example, the notification may identify the user name of the user of the first computing device, the file type, and options to download or decline the offer to share, as illustrated in a notification message 352 within a screenshot 350 of computing device 344, as illustrated in FIG. 3E.

Returning to FIG. 2, in some implementations, the second computing device 208 requests the data (224) selected by the first user to be shared with the target user(s), including the user of the second computing device 208. The request, in some implementations, includes the session identifier associated with the requested data. In some implementations, the user of the second computing device 208 may select to review the shared file (e.g., download and open the shared file) to initiate a request for the data (224). In some implementations, the user of the second computing device 208 may accept the offer to share by providing a positive response to the presented notification.

In some implementations, upon acceptance of the offer to share (e.g., positive response to the presented notification) by the user of the second computing device 208, the share service 204 requests the cached data (226) from the database 206. In some implementations, the request includes the session identifier associated with the cached data. The session identifier, in some implementations, is matched to account information stored in the database 206. In some implementations, the share service 204 retrieves the cached data (228) from the database 206 upon requesting the data and/or matching the session identifier provided by the second computing device 208 with the account information stored in the database 206.

In some implementations, the share service 204 shares the data with the target user (230) (e.g., the user of the second computing device 208). For example, upon successfully matching the session identifier to account information stored in the database 206, the share service 204 may proceed to share the data with the data share sub-application of the second computing device 208, such as the chemical structure 124 described in relation to FIG. 1.

In some implementations, the data share sub-application of the second computing device 208 causes presentation of a shared version of the data (236) within the display area of the second computing device 208. For example, as illustrated in a screen shot 360 of FIG. 3F, a shared version 308' of the chemical structure 308 provided by the computing device 302 is presented upon the computing device 344. In some implementations, a notification is presented in relation to the shared file. For example, a notification message 362 alerts the user of the computing device 344 that "CDXML file successfully imported" (as illustrated in FIG. 3F).

Returning to FIG. 2, in some implementations, the share service 204 acknowledges, to the first computing device 202, the data has been shared (234) with the second computing device 208. In some implementations, the acknowledgement includes the session identifier. In some implementations, upon receiving the acknowledgement, the first computing device 202 presents, within the display area of the first computing device 202, a notification indicative of success of sharing. For example, turning to FIG. 3C, a notification message 332 alerts the user of computing device 302 that "You successfully shared this file with Alan" (e.g., chemical structure 308 with user Alan 328a).

Figure 3A:
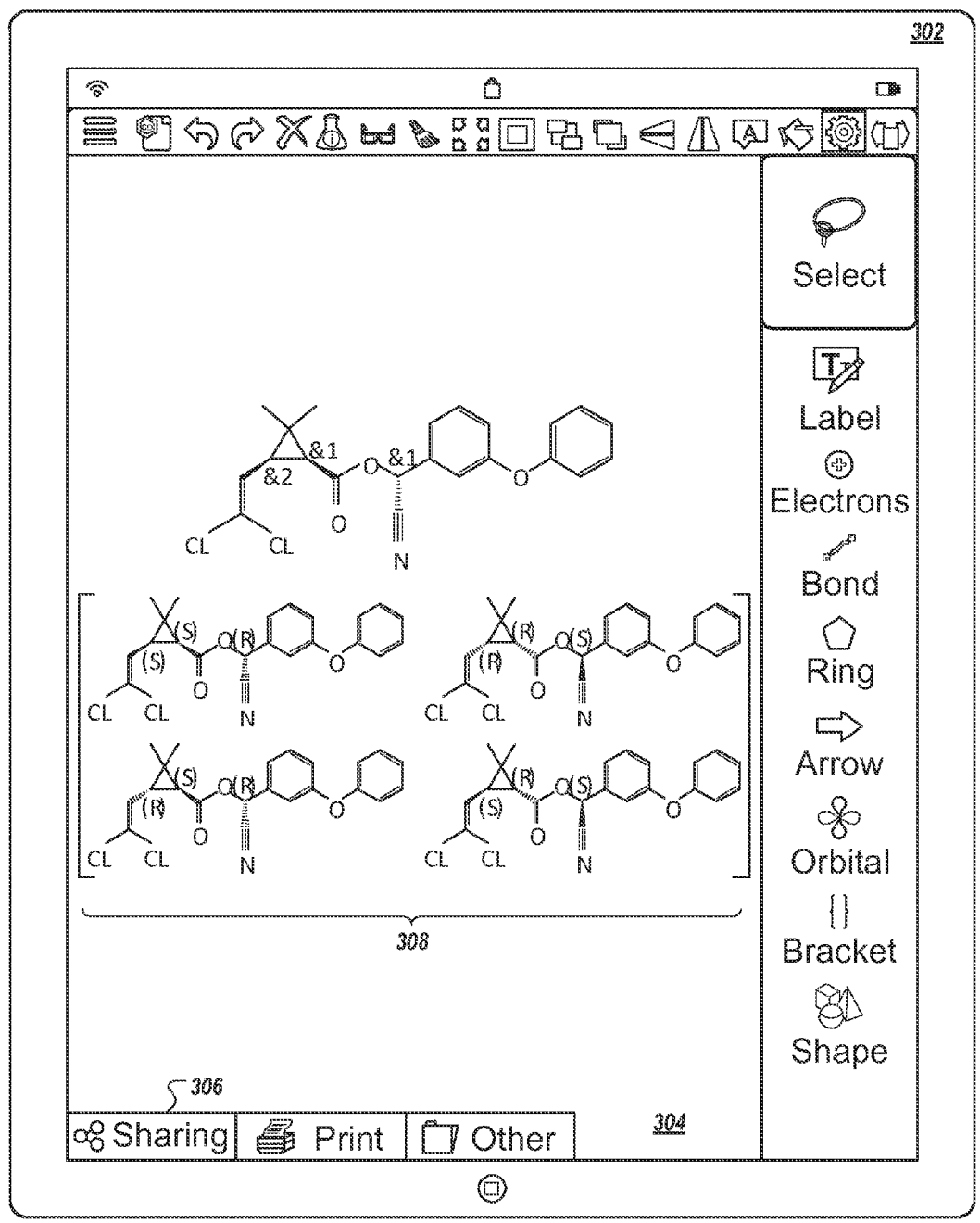
FIGS. 3A through 3F illustrate screen shots of an example data sharing operation using gesture-based sharing of a chemical structure.
Figure 3B:
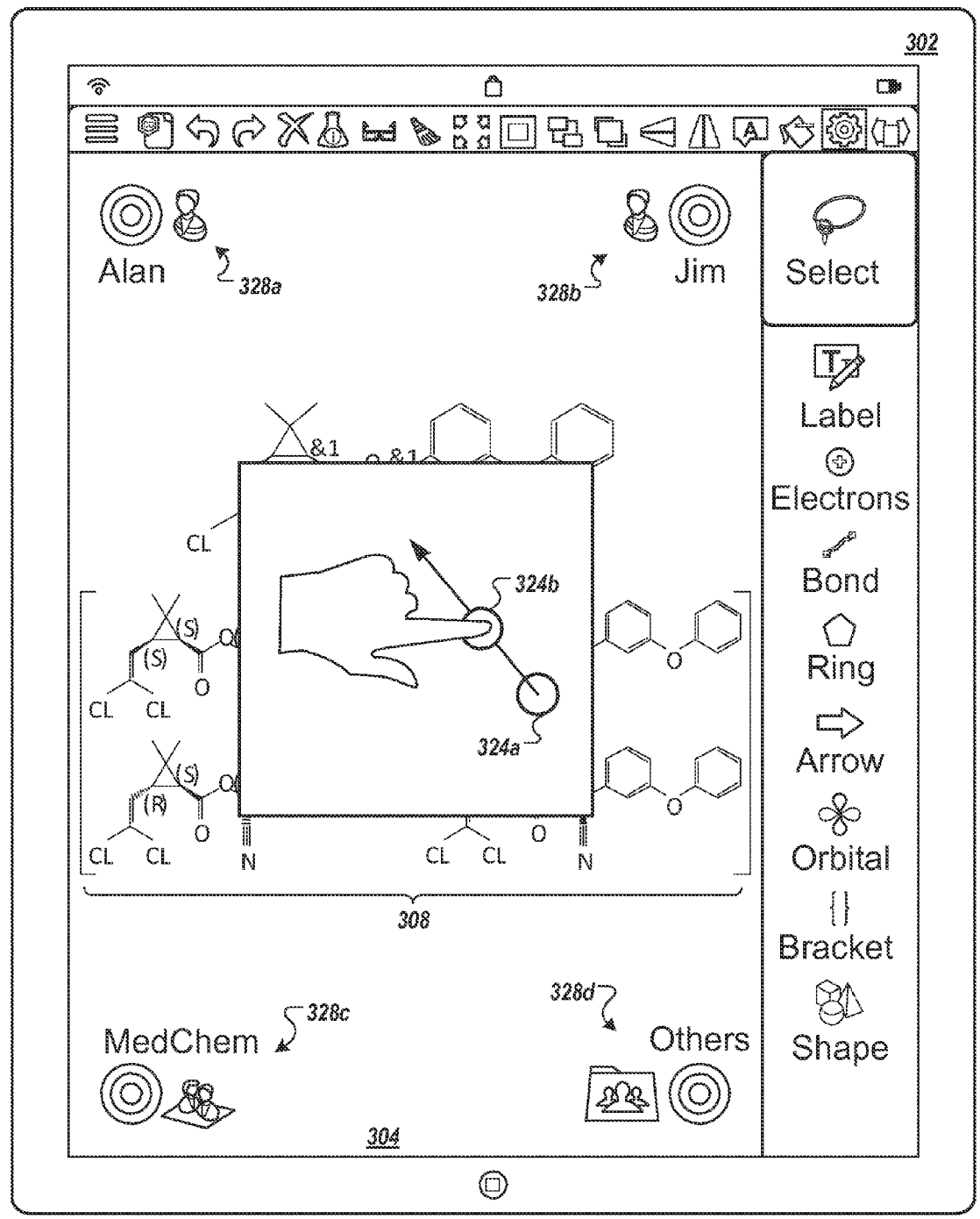
Figure 3C:
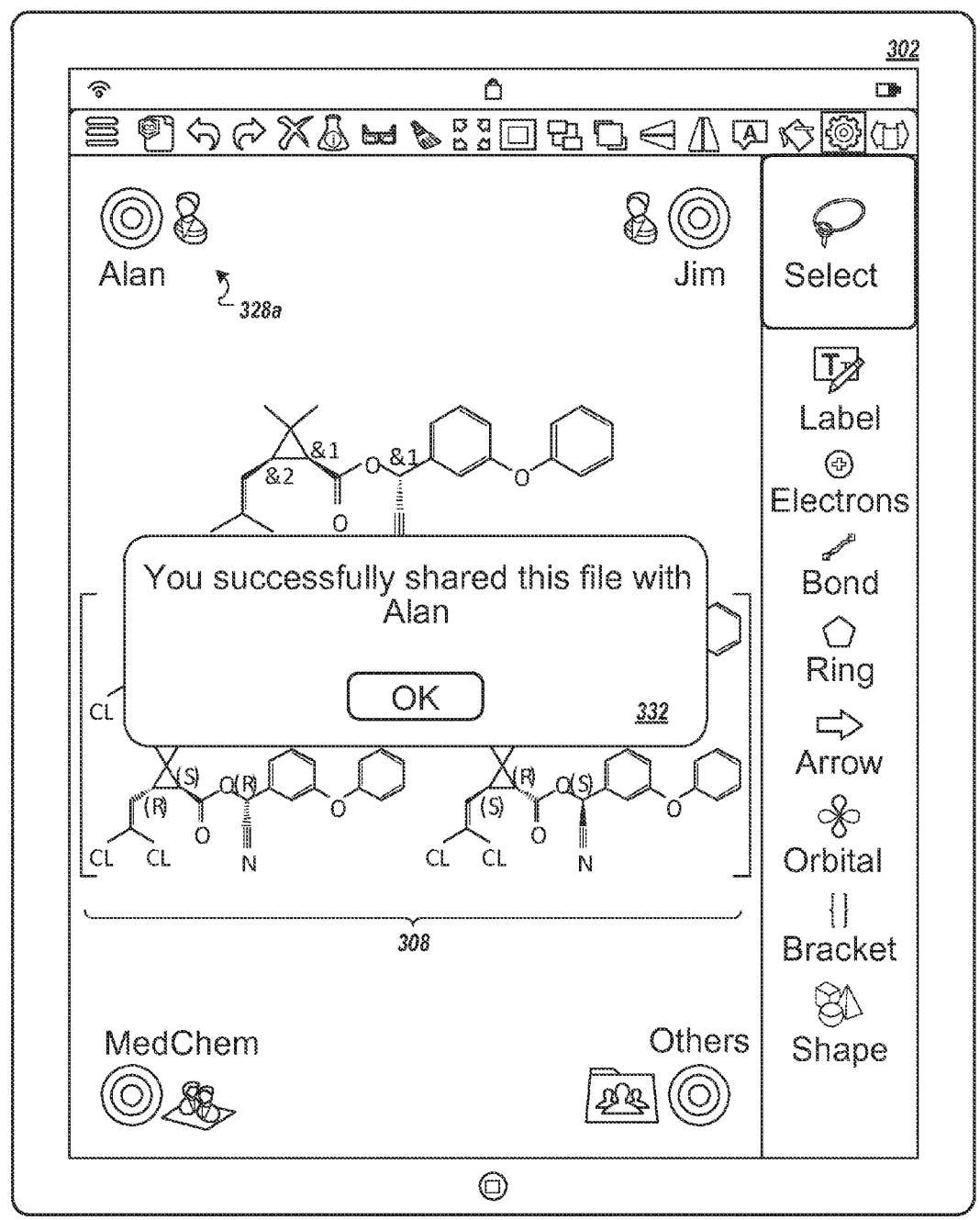
Figure 3D:
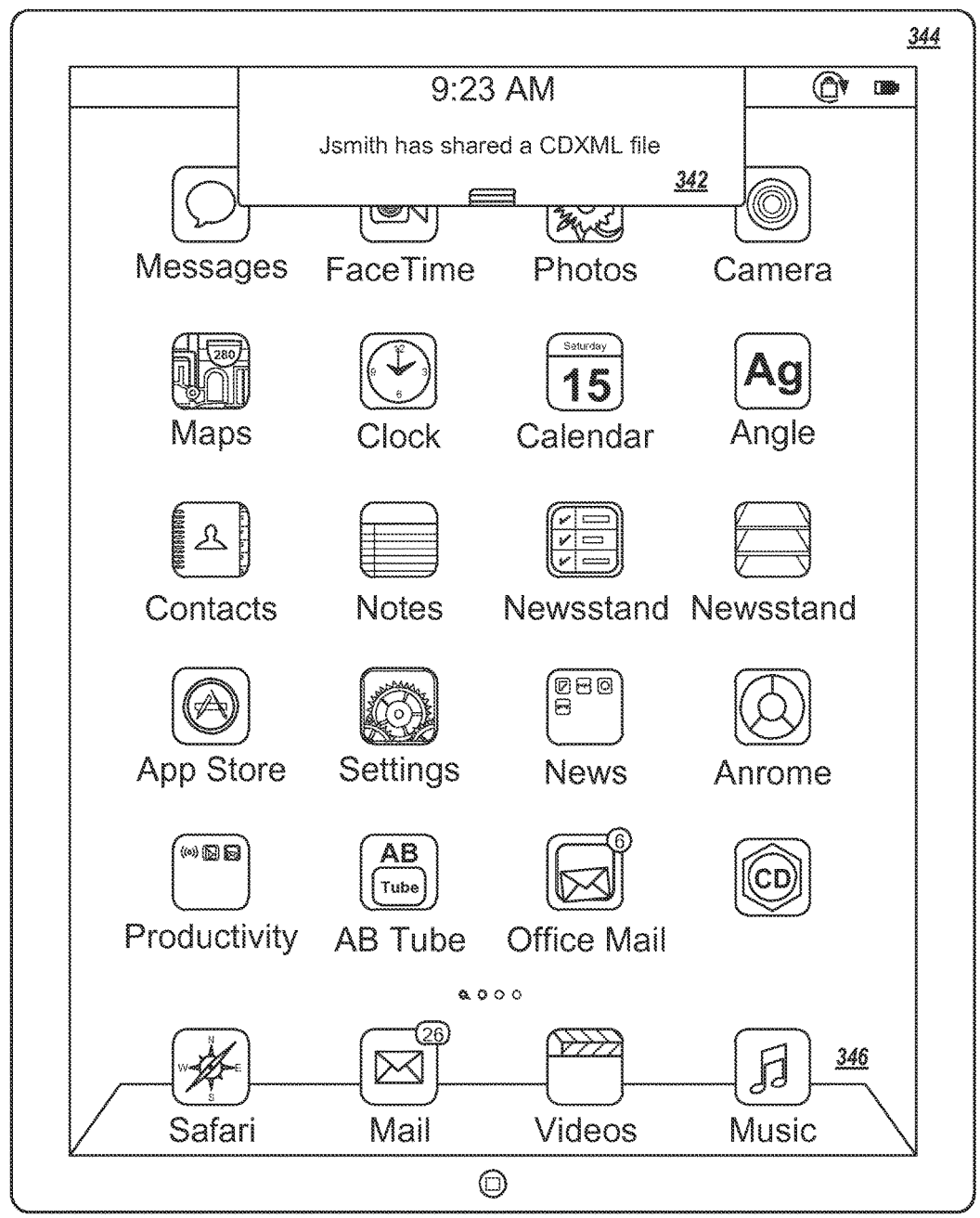
Figure 3E:
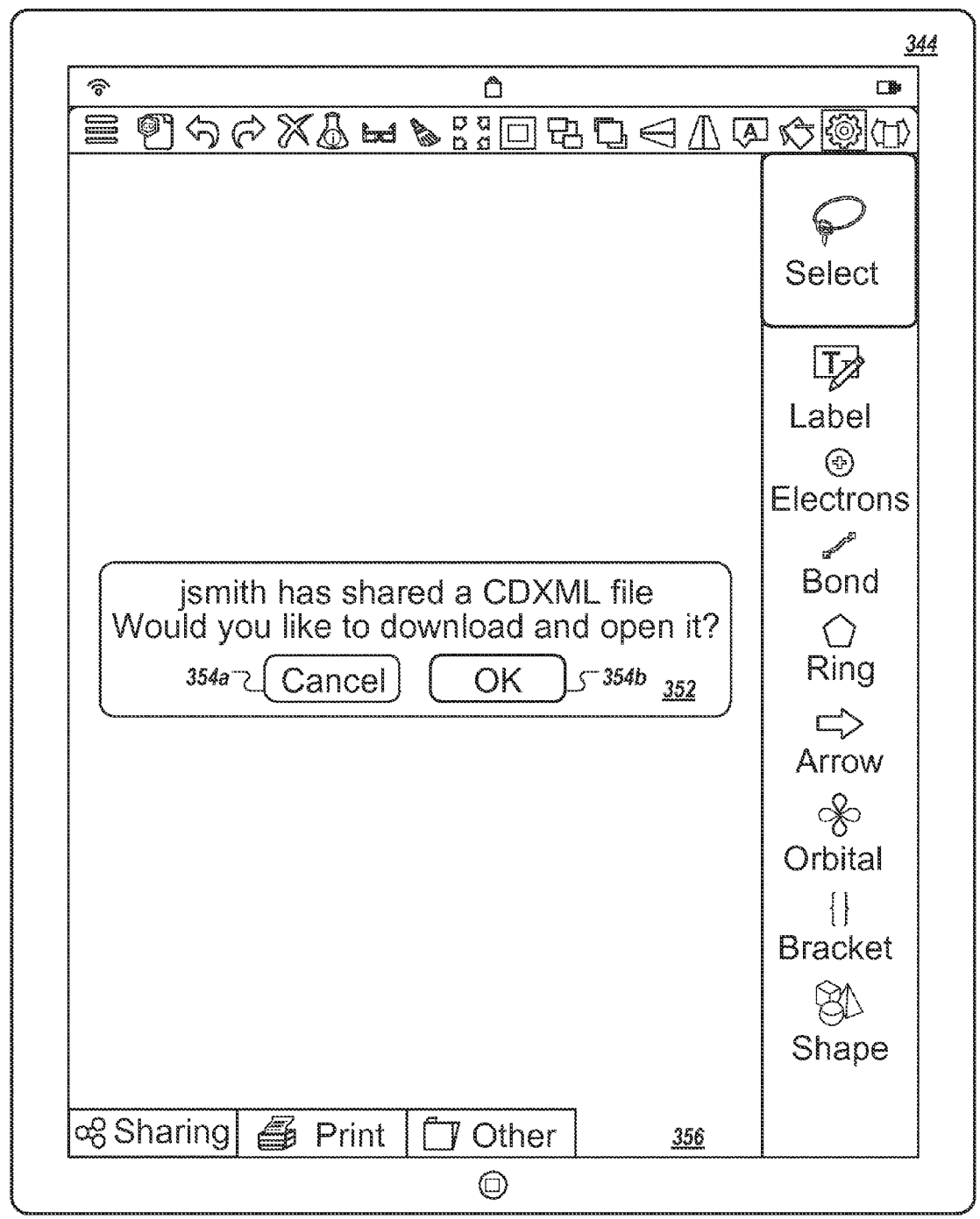
Figure 3F:
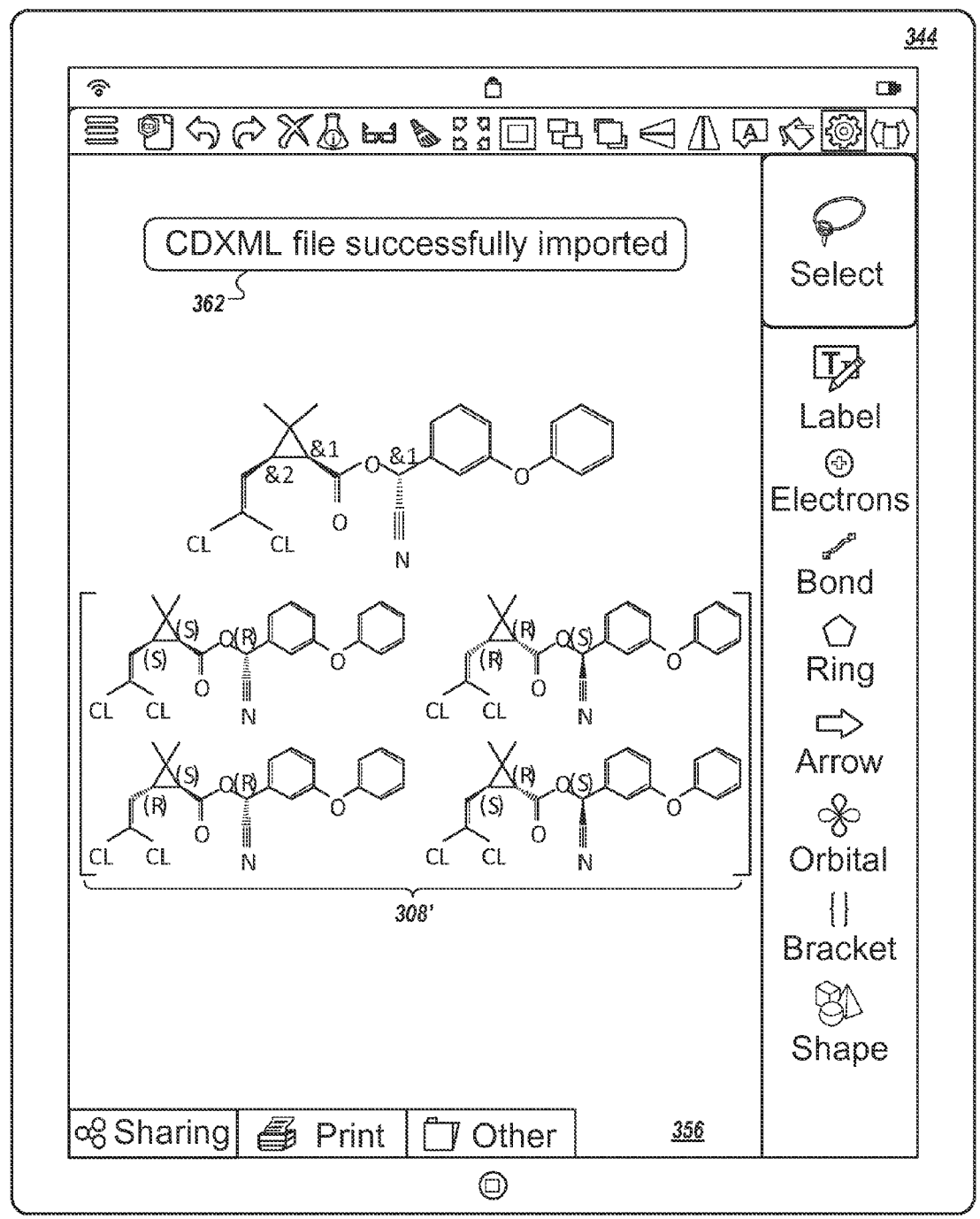

FIGS. 3A through 3F illustrate screen shots of an example data sharing operation using gesture-based sharing of a chemical structure. FIG. 3A illustrates a screen shot 300 of an example graphical user interface for performing a sharing operation using gesture-based sharing of a chemical structure. In some implementations, the first computing device includes an underlying software program that may be used to perform various functions and/or edit the underlying data via the user interface. The underlying software application, for example, may be configured for creation, editing, and/or manipulation of data files such as, in some examples, word processing software, presentation software, spreadsheet software, program development software, graphic editing software, graphical chemical structure software, graphical biological structure software, photo manipulation software, and video manipulation software.

A sharing session may be opened, in a particular example, through selecting the sharing option 306 within the display region 304, as illustrated in the screen shot 300 of FIG. 3A. In some implementations, the sharing option 306 is found within the underlying software program. In some implementations, the sharing option may be provided by a data share sub-application (e.g., as a sub-application feature layer on top of a presently executing software application), such as data share sub-application 108a of FIG. 1. In some implementations, a sharing session begins with selecting, upon the computing device 302, data to share with one or more target users. The data may include one or more files, such as the chemical structure 308. In some implementations, the sharing option 306 is selected prior to identifying the data (e.g., chemical structure 308) to share and/or the targeted user(s) with whom the data will be shared.

FIG. 3B illustrates a screen shot 320 of an example graphical user interface of the computing device 302 of FIG. 3A for performing a sharing operation using gesture-based sharing of the chemical structure 308. In some implementations, one or more members eligible for sharing the chemical structure 308, such as the chemical structure 124 as shown in FIG. 1, are displayed in the display region 304. In some implementations, a data share sub-application, such as data share sub-application 108a as shown in FIG. 1, may identify one or more members eligible for sharing the chemical structure 308. The members may be identified, in some examples, based upon one or more of a recency of sharing with the computing device 302 (e.g., same day, same week, same month, etc.), a frequency of sharing with the computing device 302, a total number of shares between the computing device 302 and a computing device associated with the respective member, an indication by the user of the computing device 302 designating the respective member as a favorite, a status of the respective member (e.g., identified by a user identifier feature of the server as being "online," "active," or otherwise available for sharing), and an indication from the user of the computing device 302 designating a particular group for sharing (e.g., engineering team, managerial team, immediate family, relatives, social club, etc.). In another example, one or more eligible members may be identified based in part upon a proximity of a computing device associated with the respective user and the computing device 302 (e.g., same room, same building, etc.). For example, the data share sub-application, through a peripheral communication feature of the computing device 302 (e.g., Bluetooth®, Wi-Fi™ NFC, etc.), may attempt to locate one or more member computing devices within range. In this manner, a user of the computing device 302 may identify team members within a conference room for sharing and collaboration. The eligible members may include non-user computing devices such as, in some examples, a printer, a facsimile, a television, a smart TV, a projector, or a media player. For example, the data share sub-application may identify, via a peripheral communication feature, nearby computing equipment configured to share files via the data share sub-application. The eligible members may include business entities such as corporations, partnerships, sole proprietorships, academic institutions, or departments or specific groups within business entities.

Out of the identified members, the data share sub-application, in some implementations, identifies a subset of the members for presentation within the display region 304. For example, the data share sub-application may identify members 328 to display radially surrounding the chemical structure 324. For example, the data share sub-application may identify up to four members 328 to display within the four corners of the display region 304.

In some implementations, to share a file with one of the members 328, the user of the first computing device 302 "pushes" the chemical structure 308 towards one or both of the graphical representations of the members 328. For example, the user may "flick" or "fling" the image of the chemical structure 308 towards the upper left corner of the display of computing device 302 with a sweeping gesture across a touch screen display (e.g., from a first point 324a to a second point 324b) to share the chemical structure 308 with user 328a. In general, a user of the computing device 302 may "push" the chemical structure 308 in the direction of any member 328 to share the chemical structure 308 with the particular member 328.

Upon performing the sweeping gesture, in some implementations, the data share sub-application illustrates the chemical structure 308 as moving across the display towards the intended member(s) 328. For example, the chemical structure 308 may be illustrated as floating or flying towards member Alan 328a. In some implementations, the chemical structure 308 may be animated as spinning, flipping, morphing, and/or shrinking while moving towards the intended member(s) 328. In some implementations, a user may press and hold chemical structure 308 to activate the "flick" feature. In some implementations, upon activating the "flick" feature, the user can drag the chemical structure 308 around the graphical user interface until the user "flicks" the chemical structure 308 to a member 328. In some implementations, a member 328 is a group of two or more members 328d. In some implementations, upon selection of member 328d, a list of other members eligible for sharing is provided in the display region 304 for selection by the user.

FIG. 3C illustrates a screenshot 330 of an example graphical user interface of the computing device 302 upon sharing the chemical structure 308 with the member Alan 328a. In some implementations, upon identifying a member with whom to share, for example, a chemical structure, as discussed in FIGS. 1 and 3B, a notification message 332 may be provided to a user of the computing device 302. The notification message 332, in some examples, may include one or more of an indication of status (e.g., acceptance or rejection of the offer to share, success or failure in file transfer, etc.), an intended member(s) (e.g., Alan, etc.), a file name, a time stamp, and information regarding the intended member(s). In a particular example, the notification may identify a user name of the user of the second computing device and an indication of status, as illustrated in the notification message 332 which reads "You successfully shared this file with Alan".

FIG. 3D illustrates a screenshot 340 of a graphical user interface of the second computing device 344 upon receipt of a shared file. In some implementations, upon receipt of the alert, as described in relation to FIGS. 1 and 2, the data share sub-application of the second computing device 344, such as data share sub-application 108b as shown in FIG. 1, presents a notification message 342 within a display region 346 (e.g., main menu view) of the second computing device 344. The notification message 342, for example, may provide the second user with the option to review the shared file (e.g., download from the server and open within a software application configured to present the indicated file type). The notification message 342, in some examples, may include one or more of a file name, a file type, information regarding the user of the first computing device 302, a file size, and a timestamp of the notification. In a particular example, the notification may identify a user name of the user of the first computing device 302, a file type, and a time of share, as illustrated in the notification message 342 in the screenshot 340 of FIG. 3D. In some implementations, the notification message 342 appears as a drop down in the display area 346. In some implementations, the notification message 342 appears regardless of which application the second computing device 344 is running when the alert is received.

In a second example, a file share notification message may identify the user name of the user of the first computing device, the file type, and options to download or decline the offer to share, as illustrated in a notification message 352 within a screenshot 350 of FIG. 3E. Turning to FIG. 3E, in some implementations, the notification message 352 is presented as a pop-up window. The notification message 352 indicates to the user of the computing device 344 "jsmith has shared a CDXML file" as well as "Would you like to download and open it?" The user is further presented with controls 352 configured to allow the user of the computing device 344 to accept or decline the offer to share the CDXML file from jsmith.

FIG. 3F illustrates an example screenshot 360 of a graphical user interface of the second computing device 344, confirming a shared version of the chemical structure 308 (as illustrated, for example, within the display region 304 of the first computing device 302 in FIG. 3B) has been successfully imported by the second computing device 344. In some implementations, the notification message 362 is presented in a display region 356 of the second computing device 344. The notification message 362 confirms the file was successfully imported, as identified in the message "CDXML file successfully imported".

FIGS. 4A through 4D illustrate screen shots of an example data sharing operation for sharing multiple files using gesture-based sharing of a chemical structure. In some implementations, an underlying software application 404 operates on a first computing device 402 illustrated in screen shot 400 in FIG. 4A. In some implementations, the underlying software application 404 provides, in one example, one or more chemical structures 406. The underlying software application 404, for example, may be configured for creation, editing, and/or manipulation of data files such as, in some examples, word processing software, presentation software, spreadsheet software, program development software, graphic editing software, graphical chemical structure software, graphical biological structure software, photo manipulation software, and video manipulation software.

Figure 4A:
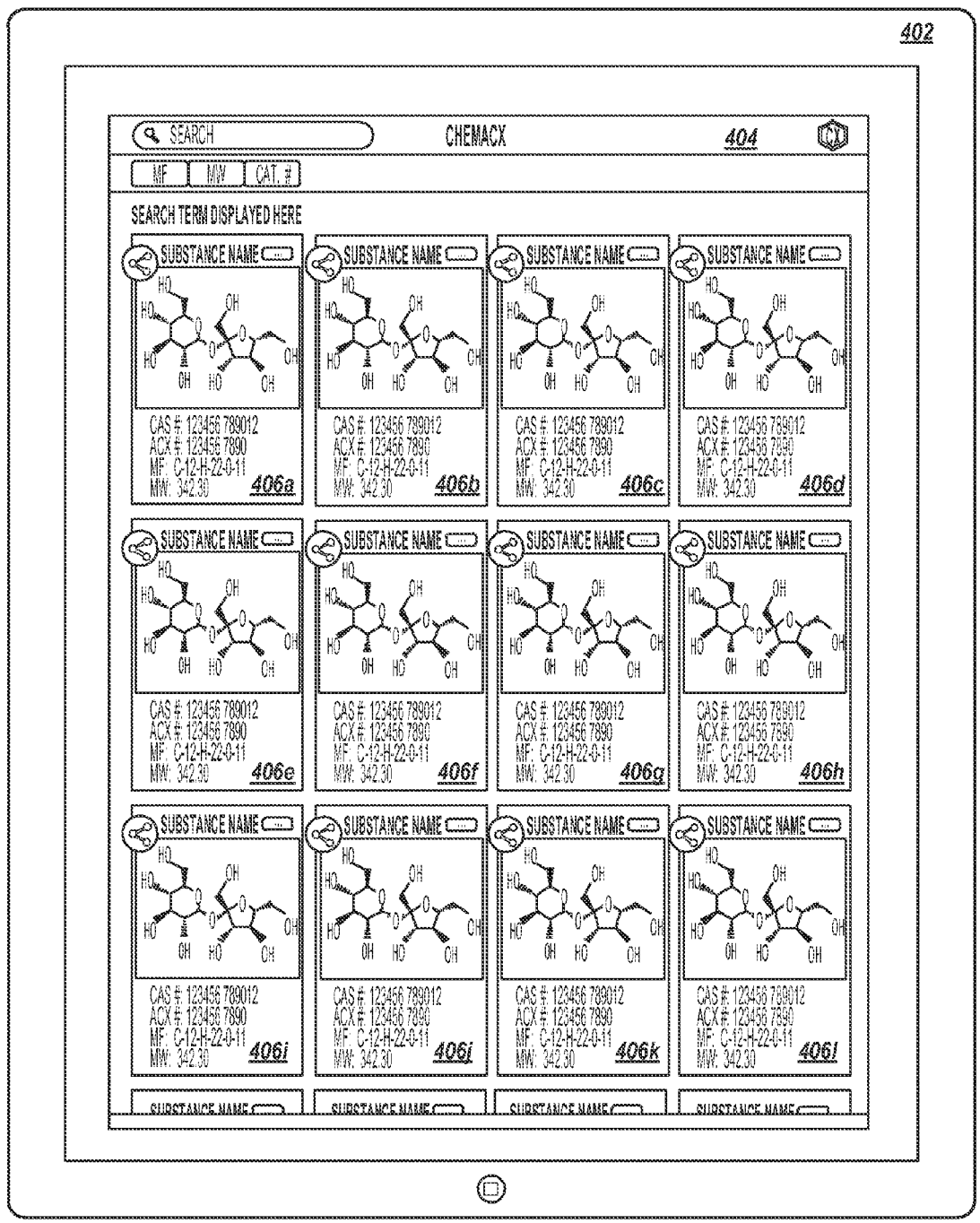
FIGS. 4A through 4D illustrate screen shots of an example data sharing operation for sharing multiple chemical structure renderings.
Figure 4B:
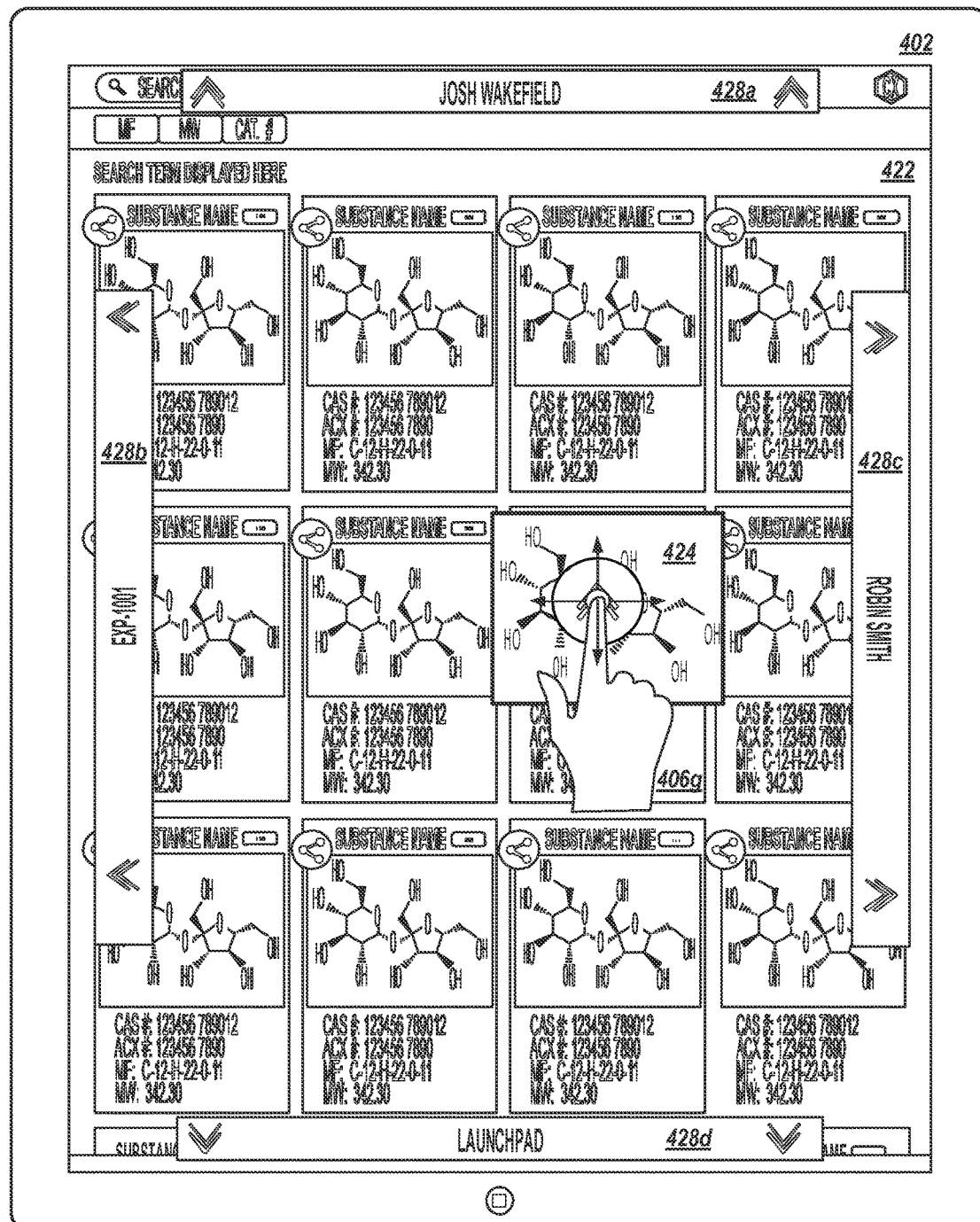

FIG. 4B illustrates a screenshot 420 of an example data sharing operation using gesture-based sharing of a chemical structure. In some implementations, a sharing session may be opened, in a particular example, through selecting a sharing option within a user interface of the first computing device 402. In some implementations, a sharing option may be initiated by selecting and/or holding 424 the file the user wishes to share, such as, for example, chemical structure 406g.

In some implementations, one or more members eligible for sharing the chemical structure 406g, such as the chemical structure 124 as shown in FIG. 1, are displayed within a display region 422. In some implementations, a data share sub-application, such as data share sub-application 108a as described in relation to FIG. 1, may identify one or more members eligible for sharing the chemical structure 406g. The members may be identified, in some examples, based upon one or more of a recency of sharing with the computing device 402 (e.g., same day, same week, same month, etc.), a frequency of sharing with the computing device 402, a total number of shares between the computing device 402 and a computing device associated with the respective member, an indication by the user of the computing device 402 designating the respective member as a favorite, a status of the respective member (e.g., identified by a user identifier feature of the server as being "online," "active," or otherwise available for sharing), and an indication from the user of the computing device 402 designating a particular group for sharing (e.g., engineering team, managerial team, immediate family, relatives, social club, etc.). In another example, one or more eligible members may be identified based in part upon a proximity of a computing device associated with the respective user and the computing device 402 (e.g., same room, same building, etc.). For example, the data share sub-application, through a peripheral communication feature of the computing device 402 (e.g., Bluetooth®, Wi-Fi™ NFC, etc.), may attempt to locate one or more member computing devices within range. In this manner, a user of the computing device 402 may identify team members within a conference room for sharing and collaboration. The eligible members may include non-user computing devices such as, in some examples, a printer, a facsimile, a television, a smart TV, a projector, or a media player. For example, the data share sub-application may identify, via a peripheral communication feature, nearby computing equipment configured to share files via the data share sub-application. The eligible members may include business entities such as corporations, partnerships, sole proprietorships, academic institutions, or departments or specific groups within business entities.

Out of the identified members, the data share sub-application, in some implementations, identifies a subset of the members for presentation within the display region 422. For example, the data share sub-application may identify members 428 to display radially surrounding the chemical structure 406g. In particular, the data share sub-application may identify up to four members 428 to display along the four edges of the display region 422, as illustrated in a screen shot 420 of FIG. 4B.

The identified members, in some implementations, do not necessarily correspond to a user of a computing device. For example, member EXP-1001 428b may refer to a particular piece of laboratory equipment, document rendering equipment (e.g., printer, facsimile, etc.) or data presentation equipment (e.g., projector, television, smart TV, etc.). In another example, member Launchpad 428d may refer to a "member" that allows for selection of two or more files for sharing at once with one or more target members.

Figure 4C:
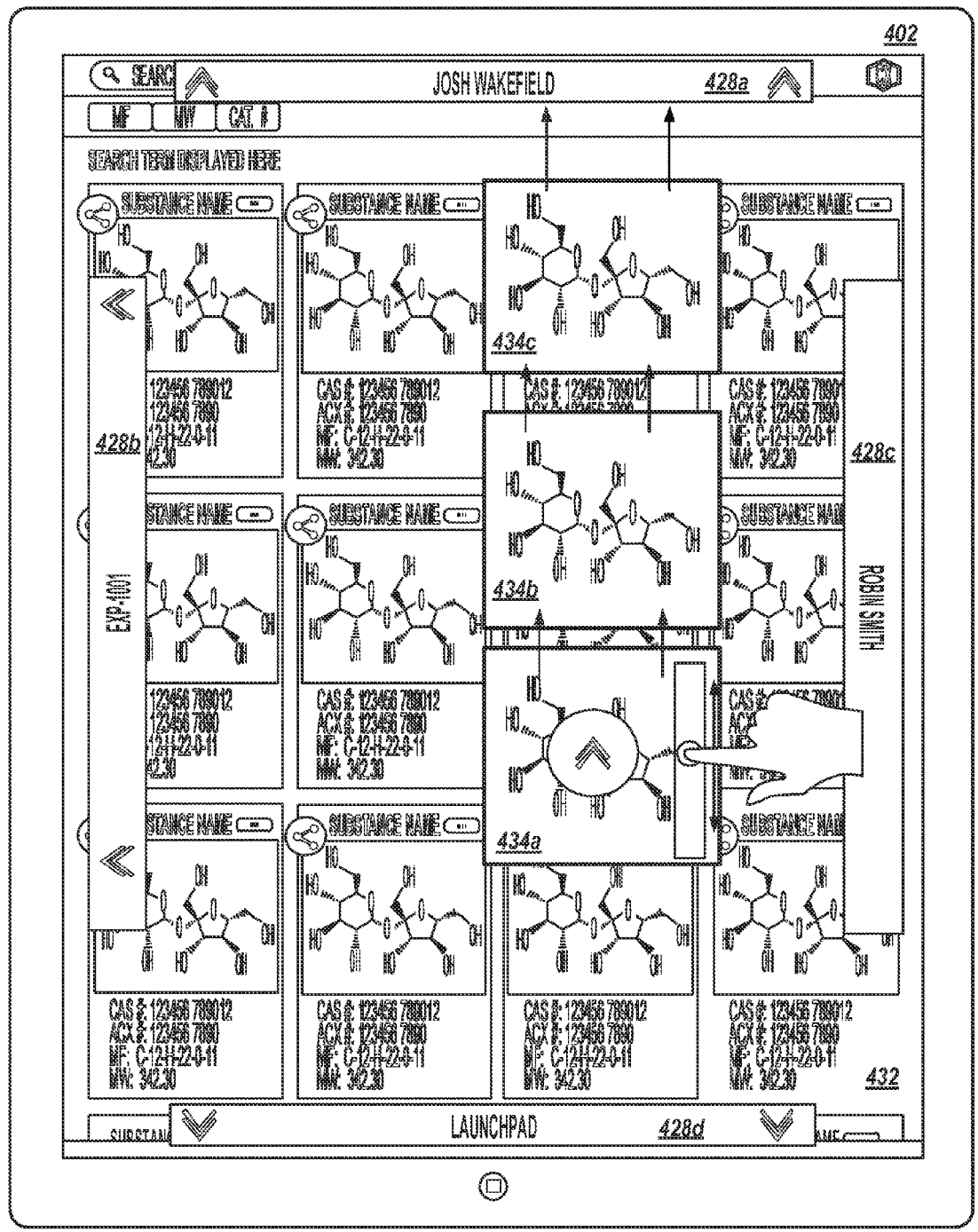

FIG. 4C illustrates a screenshot 430 of the computing device 402 demonstrating a data sharing operation using gesture-based sharing. In some implementations, to share a file with one of the members 428, the user of the first computing device 402 "pushes" a selected chemical structure (e.g., chemical structure 406g as illustrated in reference to FIG. 4B) towards one or more graphical representations of the members 428. For example, the user may "flick" or "fling" the image of the chemical structure 406g towards the top of the display of computing device 402 with a sweeping gesture across a touch screen display to share the chemical structure 406g with user 428a. In another example, the user may "flick" or "fling" the image of the chemical structure 406g towards the top of the display with a sweeping gesture made using a wearable computing device such as computerized eye glasses, a stylus, or another input device.

Upon performing the sweeping gesture, in some implementations, the data share sub-application illustrates the chemical structure a graphical representation 434 of the chemical structure 406g as moving across the display towards the intended member 428a. For example, the graphical representation 434 may be illustrated as floating or flying (e.g., in stages 434a, 434b, and 434c) towards member Josh Wakefiled 428a. In some implementations, the graphical representation 434 may be animated as spinning, flipping, morphing, and/or shrinking while moving towards member Josh Wakefiled 428a.

Figure 4D:
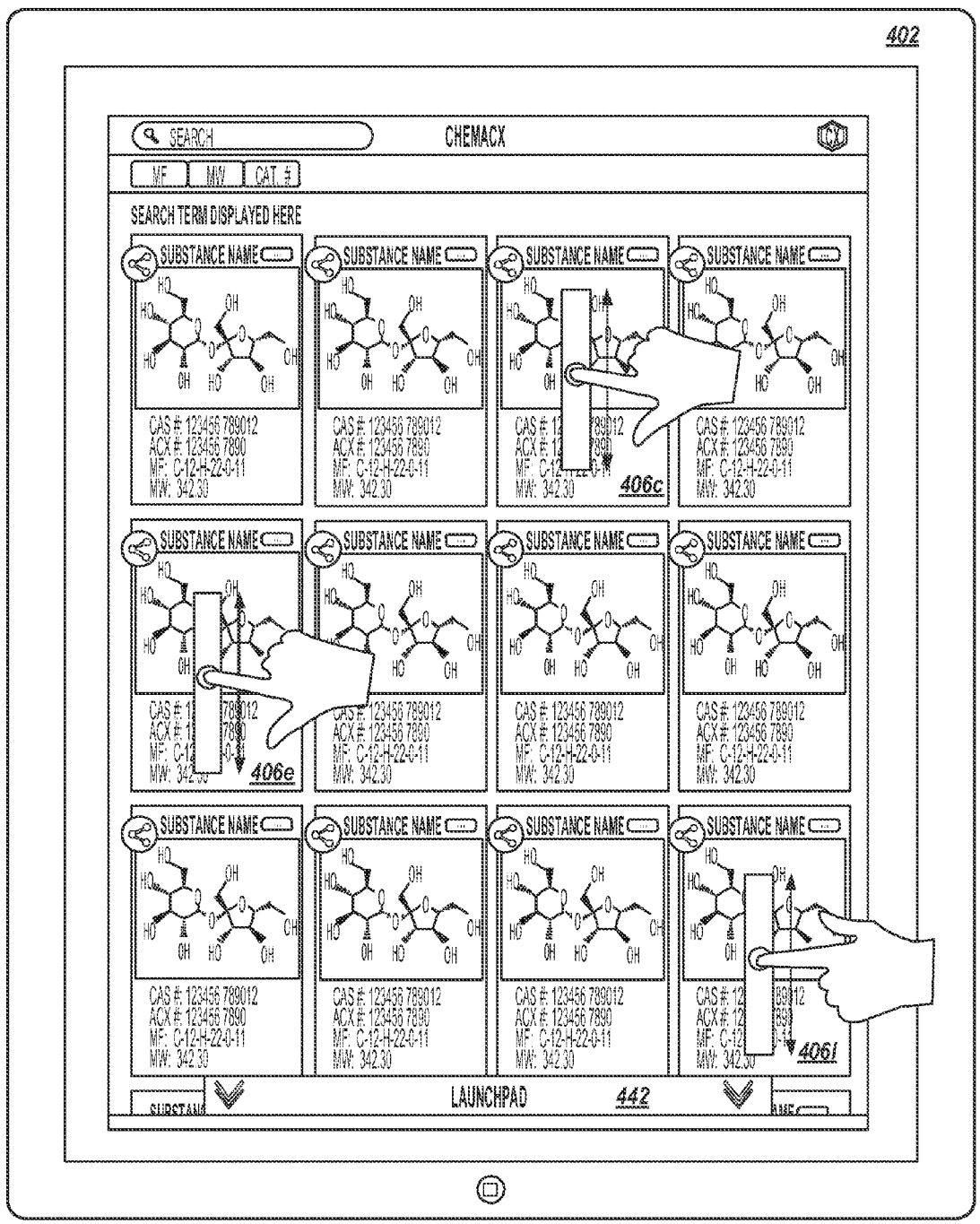

FIG. 4D illustrates an example screenshot 440 of a graphical user interface on the computing device 402 for sharing multiple chemical structure renderings. The user of computing device 402 may "push" one or more chemical structures 406 towards the launch pad 442. In some implementations, the launch pad 442 is activated when a user selects or swipes upon the launch pad. In some implementations, launch pad is activated when a user "pushes" a chemical structure 406 to the launch pad 442. In some implementations, upon activation of the launch pad 442, a launch pad interface is displayed on the computing device 402. The launch pad interface may allow a user to view a collection of one or more chemical structures that have been sent to the launch pad 442 for sharing with one or more members. In some implementations, the launch pad 442 provides a graphical user interface that enables a user of the computing device 402 to identify members with whom the user would like to share one or more of the chemical structures on the launch pad 442.

Figure 5:
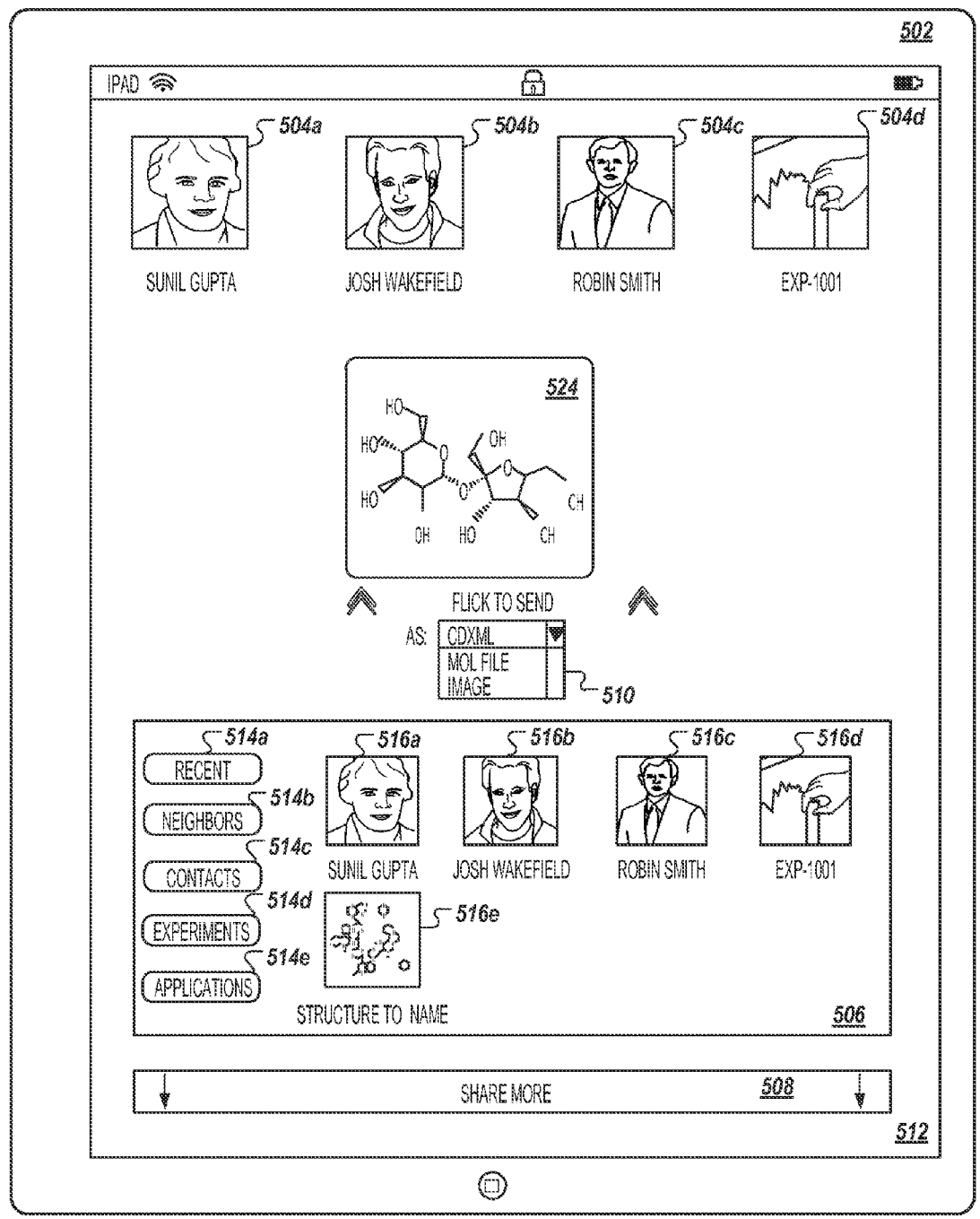
FIG. 5 is a screen shot of an example graphical user interface for identifying one or more recipients in a gesture-based data sharing operation.

FIG. 5 is a screen shot 500 of an example graphical user interface for identifying one or more recipients in a gesture-based data sharing operation on a computing device 502. In some implementations, a display region 512 of the computing device 502 includes one or more files, such as chemical structures 524 previously identified (e.g., selected) by the user of the computing device 502 for sharing with one or more target members. In some implementations, as described in relation to FIG. 1, a user may "push" the chemical structure 524 towards one or more members 504 to share the chemical structure 524.

In some implementations, the user is presented with two or more file format options 510 for sharing data such as the chemical structure 524. For example, as illustrated within the display area 512 of the computing device 502, the user of a computing device 502 can choose to share the chemical structure 524 as a variety of file types such as a CDXML file, a MOL file, or an image file. The chemical structure 524, for example, may be loaded presently as a CDXML file. Selection of a different file type 510, in some implementations, causes conversion of the chemical structure 524 into a different file type prior to sharing. The data share sub-application, such as 108a as shown in FIG. 1, for example, may call into a "save as" function of the presently executing software application (e.g., a chemical structure drawing and manipulation program) to modify the file type of the chemical structure 524 prior to sharing with other users.

In some implementations, the data share sub-application determines a file type for sharing based in part upon the capabilities of member computing devices, such as the computing device of the member with whom the user of the computing device 502 wants to share the chemical structure 524. For example, if the computing device of the member has an image file presentation application installed, but no chemical structure drawing and manipulation program, the data share sub-application of the computing device 502 may identify that the chemical structure 524 should be converted to an image file prior to sharing with the computing device of the target member. The data share sub-application, executing upon the computing device of the member, in some implementations, indicates to a server, such as server 110 as shown in FIG. 1, a list of eligible file types (e.g., file types renderable by one or more applications interfacing with, for example, a data share sub-application such as data share sub-application 108*b* as shown in FIG. 1). The server, in turn, may provide this information to the computing device 502, for example, upon presentation of the members 504.

A data share sub-application, such as data share sub-application 108*a* as shown in FIG. 1, executing upon the computing device 502, may identify one or more members 504 eligible for sharing the chemical structure 524, as described, for example, with reference to FIG. 1. In some implementations, the data share sub-application may arrange two or more members along a single edge of the display region 512 of the first computing device 502 as illustrated in relation to FIG. 5. The user of the computing device 502 may use a contacts panel 506 to add additional members to the upper display area (e.g., the members 504 along the top edge of the display area) where the user may then share the chemical structure 524 with the members 504.

In some implementations, the members with whom the user of the first computing device 502 would like to share the chemical structure 524 with are displayed at the upper display area (e.g, members 504). In some implementations, the contact panel displays one or more contacts with whom the user may share the chemical structure 524. In some implementations, the user of the first computer device 502 may remove a member 504, such as member 504*a*, by "pushing" member 504*a* to the contacts panel 506. In some implementations, the user can adjust the members shown in contacts panel 506 by selecting the category 514 of members the user would like to see, such as recent, neighbors 514*a*, contacts 514*b*, experiments 514*c*, peripherals 514*d*, and applications 514*e*. The user, in some implementations, can be presented with one or more members of a particular category 514 within the upper area of the display region 512 upon selection of the particular category 514. For example, upon selection of the category neighbors 514*b*, the present members 504*a* through 504*d* may be replaced with one or more target members categorized as neighbors. A particular member, in some implementations, may belong to two or more categories. For example, member Sunil Gupta 514*a* may belong to both the recent category 514*a* and the contacts category 514*c*. In some implementations, the user may share with members in the contacts panel 506 by "pushing" the chemical structure 524 to the graphical representations of a member 516 in the contacts panel 506.

The members may be identified, in some examples, based upon one or more of a recency of sharing with the computing device 502 (e.g., same day, same week, same month, etc.), a frequency of sharing with the computing device 502, a total number of shares between the computing device 502 and a computing device associated with the respective member, an indication by the user of the computing device 502 designating the respective member as a favorite, a status of the respective member (e.g., identified by a user identifier feature of the server as being "online," "active," or otherwise available for sharing), and an indication from the user of the computing device 502 designating a particular group for sharing (e.g., engineering team, managerial team, immediate family, relatives, social club, etc.). In another example, one or more eligible members may be identified based in part upon a proximity of a computing device associated with the respective user and the computing device 502 (e.g., same room, same building, etc.). For example, the data share sub-application, through a peripheral communication feature of the computing device 502 (e.g., Bluetooth®, Wi-Fi™, NFC, etc.), may attempt to locate one or more member computing devices within range. In this manner, a user of the computing device 502 may identify team members within a conference room for sharing and collaboration. In some implementations, eligible members can include non-user computing devices such as, in some examples, a printer, a facsimile, a television, a smart TV, a projector, or a media player. For example, the data share sub-application may identify, via a peripheral communication feature, nearby computing equipment configured to share files via the data share sub-application.

In some implementations, the user of the computing device 502 may select a share more option 508. The share more option 508 may provide the user with a graphical user interface, such as the graphical user interface shown in FIG. 3A or 4A, where the user may select one or more, for example, chemical structures to share with one or more members.

Figure 6A:
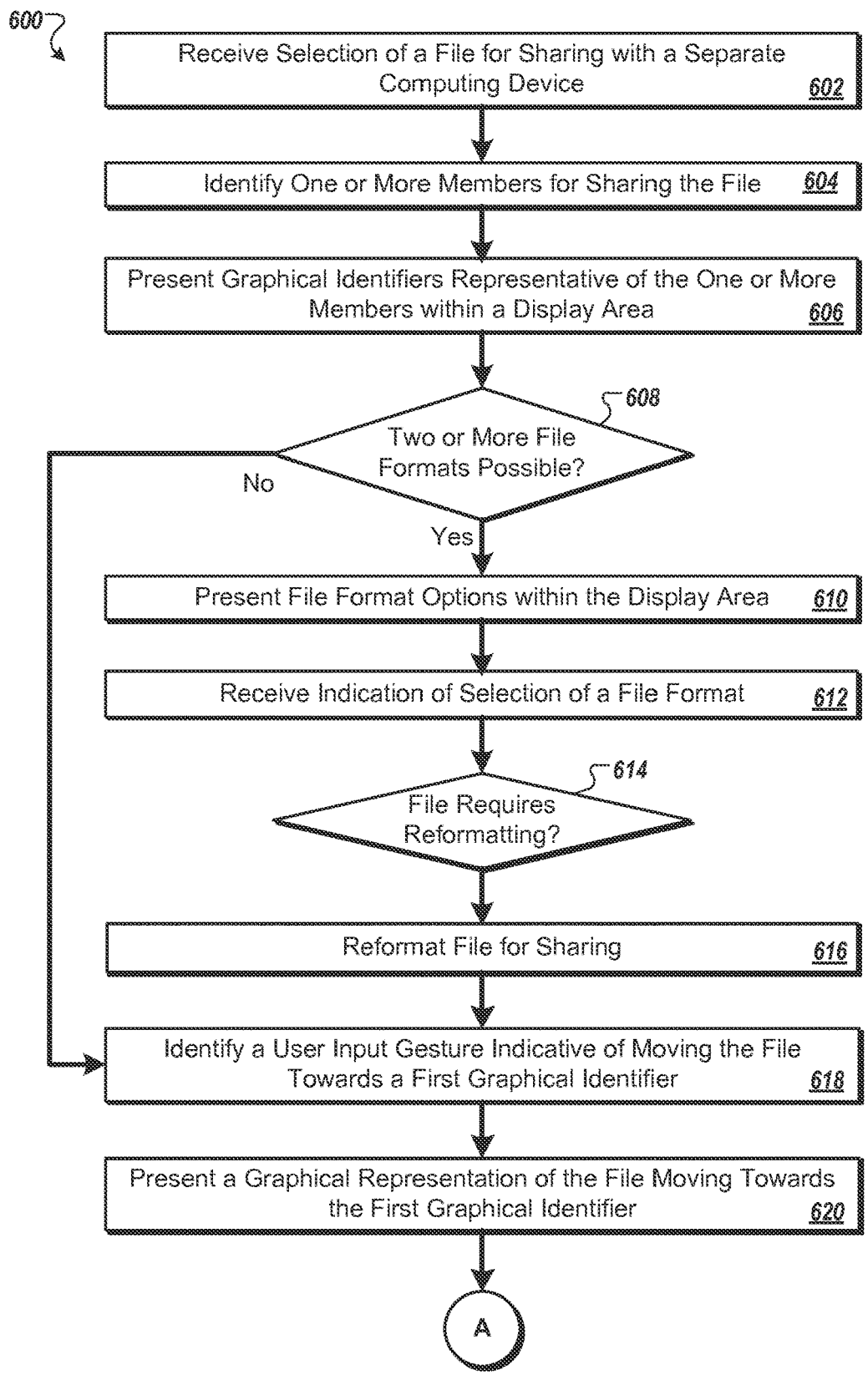
FIGS. 6A and 6B illustrate a flow chart of an example method for gesture-based sharing of data between computing devices.
Figure 6B:
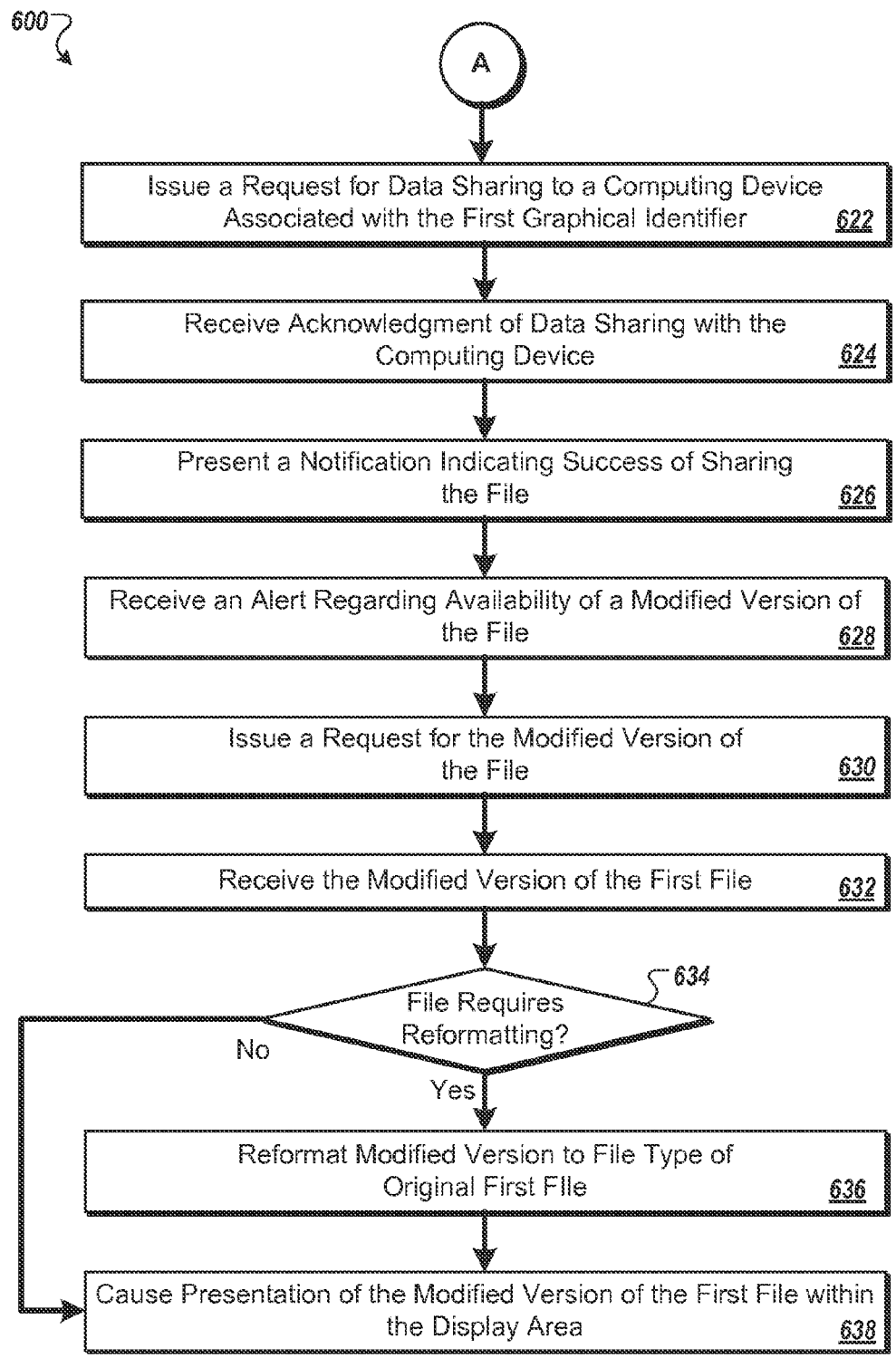

FIGS. 6A and 6B illustrate a flow chart of an example method 600 for gesture-based sharing of data between computing devices. The method, for example, may be performed by the sub-application 108, as described in relation to FIG. 1.

In some implementations, the method 600 begins with receiving, via a user interface, selection of at least one file for sharing with a separate computing device (602). Receiving selection of the at least one file may include identifying a user input gesture indicative of selection of the at least one file. The file may be selected within a software application. The method may be performed by a sub-application configured to execute within the software application. The sub-application may be configured to execute within two or more software applications installed upon the computing device.

In some implementations, the method 600 includes identifying one or more members for sharing the at least one file (604). Identifying one or more members for sharing may include issuing, via the network, an availability request and, responsive to the availability request, receiving indication of one or more member identifiers. Each member identifier may be associated with a respective computing device executing a sharing sub-application in communication with the network.

The members may be identified, in some examples, based upon one or more of a recency of sharing with the computing device (e.g., same day, same week, same month, etc.), a frequency of sharing with the computing device, a total number of shares between the computing device and a computing device associated with the respective member, an indication by the user of the computing device designating the respective member as a favorite, a status of the respective member (e.g., identified by a user identifier feature of the server as being "online," "active," or otherwise available for sharing), and an indication from the user of the computing device designating a particular group for sharing (e.g., engineering team, managerial team, immediate family, relatives, social club, etc.). In another example, one or more eligible members may be identified based in part upon a proximity of a computing device associated with the respective user and the computing device (e.g., same room, same building, etc.). For example, the application, through a peripheral communication feature of the computing device (e.g., Bluetooth®, Wi-Fi™, NFC, etc.), may attempt to locate one or more member computing devices within range. In this manner, a user of the computing device may identify team members within a conference room for sharing and collaboration. In some implementations, eligible members can include non-user computing devices such as, in some examples, a printer, a facsimile, a television, a smart TV, a projector, or a media player. For example, the application may identify, via a peripheral communication feature, nearby computing equipment configured to share files via the application.

In some implementations, the method 600 includes presenting of one or more graphical identifiers within a display area of the computing device (606). Each graphical identifier may be representative of a respective member of the members identified for sharing. The identifiers may represent a portion of the members identified for sharing. The portion of the members represented may be based on or partially based on frequency, recency of file sharing with the computing device, and/or co-location of the computing device with respective computing devices of members. The co-location of the two devices may be based in part upon near field communications. In some implementations, each graphical identifier includes a name, an icon, and/or an image associated with the respective member represented by the respective graphical identifier. In some implementations, the graphical identifiers are arranged radially surrounding a graphical representation of the file(s) the user wants to share.

In some implementations, the method 600 includes determining if two or more file formats are possible (608). The application may determine a file type for sharing based in part upon the capabilities of member computing devices. For example, if the computing device of the member with whom the user would like to share the file has an image file presentation application installed, but not a chemical structure drawing and manipulation program, the application may identify that the file, such as a chemical structure, should be converted to an image file prior to sharing with the member's computing device. The application, executing upon the member's computing device, in some implementations, indicates to a server a list of eligible file types (e.g., file types renderable by one or more applications interfacing with a local share application). The server, in turn, may provide this information to the first computing device, for example, upon presentation of the members.

If two or more file formats are possible (608), in some implementations, the method includes presenting, to a user, two or more file format options for sharing file (610) such as the chemical structure as shown in FIG. 1. The application, for example, may call into a "save as" function of the presently executing software application (e.g., a chemical structure drawing and manipulation program) to modify the file type of the file prior to sharing with members identified for sharing by the user.

In some implementations, the method 600 includes receiving, responsive to presentation of the file format options (610), an indication of the selection of the file format (612). The method 600, in some implementations, includes determining whether the file requires reformatting (614) and subsequently formatting the file if formatting is required (616).

In some implementations, the method 600 includes identifying a user input gesture indicative of moving the file towards a first graphical identifier (618) responsive to identifying the user input gesture. The identifying the user input gesture may include identifying a sweeping gesture across a touch screen. For example, the user may "flick" or "fling" the data to be shared (e.g., touch gesture on a touch screen, stylus gesture, sweeping gesture made with a wearable computing device such as computerized glasses, etc.) towards one or more graphical representations of users with whom the user wishes to share the data. In another example, the user may pull back and release on a graphical representation of the data like releasing a sling shot.

In some implementations, the method 600 includes, upon identifying a user input gesture indicative of moving the file towards a graphical identifier, presenting a graphical representation of the at least one file moving towards the at least the first graphical identifier (620). For example, the file may be illustrated as floating or flying towards the intended member(s). In some implementations, the file may be animated as spinning, flipping, morphing, and/or shrinking while moving towards the intended member(s).

In some implementations, the method 600 includes issuing, via a network, a request for data sharing to a computing device associated with the first graphical identifier (622). The request for data sharing may include a member identifier associated with the first graphical identifier. The request for data sharing may include information associated with the at least one file. The information associated with the file may include an identification of a network file location.

In some implementations, the method 600 includes receiving, via the network, responsive to the request for data sharing, an acknowledgment of data sharing (624). The acknowledgment may include the member identifier. In some implementations, the method 600 includes, responsive to receiving the acknowledgment, causing presentation, within the display area, of a notification indicative of success of sharing (626). The notification, in some examples, may include one or more of an indication of status (e.g., acceptance or rejection of the offer to share, success or failure in file transfer, etc.), an intended member, a file name, a time stamp, and information regarding the intended member. An example of a notification indicative of success of sharing is shown in FIG. 3C (e.g., notification 332).

In some implementations, the method 600 includes, after receiving the acknowledgement, receiving, via the network, an alert regarding data availability (628). The alert may be associated with a modified version of a first file of the at least one file. The alert may include a session identifier. The session identifier may be used to identify the file and/or users with who the file is shared. The session identifier may be used to identify, to the user who receives the alert, the file that has been modified, the users with whom the file is shared, and/or the user that modified the file. For example, a group of users may be using, viewing, and/or modifying a particular file during a given period of time. Users within the group may receive notifications when the file is modified. In some implementations, one or more users of the group may be alerted of modification based upon the modifying member initiating a share operation.

The method 600 may include issuing, via the network, responsive to the alert, a request for the modified version of the first file (630). The request for the modified version of the first file may include the session identifier. For example, the users in the group from the previous example may request the user who modified the file share the file with them and/or the rest of the group. The method 600 may also include receiving, via the network, the modified version of the first file (632).

The method 600, in some implementations, includes determining whether the modified file requires reformatting (634) and subsequently formatting the modified file (636) if formatting is required. In some implementations, the modified format will be reformatted to a file type that is viewable by the user. The file may be reformatted to the file type of the original first file if the user requesting the modified version has the software necessary to view the file type of the original first file. In some implementations, the user's preferred file type for a particular file may be stored and the file may be automatically converted when the user requests the modified version. In some implementations, the user selects the desired file type for the modified version.

In some implementations, the method 600 includes presenting the modified version of the first file within the display area of the computing device of the user that requested the modified version of the first file (638). The presentation of the modified version of the first file may include an indication of the member who originally created the file, members who subsequently modified the file, and/or the member who is responsible for the most recent modification of the file. In some implementations, an indication of the members who modified the first file are presented in the display area of the computing device and the user of the computing device can select the members who modified the first file to see the modifications that each user made to the file.

Although described as a particular series of steps, in other implementations, the method 600 may be performed with more or fewer steps, or some of the steps of the method 600 may be performed in a different order. For example, in some implementations, one or more members may be identified (604) and presented within the display area (606) prior to selection of a file for sharing (602). In another example, in some implementations, rather than receiving a request regarding availability of a modified version of a file, the request may identify availability of a file (as though it is a completely different file). The user, upon presentation of the modified version of the first file, may be presented with the opportunity to "link" the modified version with the original version of the file (e.g., overwrite, save as a new version, etc.). Other modifications of the method 600 are possible.

In some implementations, the system is implemented with a cloud computing system. An underlying application or a data sharing sub-application, as described in relation to FIG. 1, may interact with a cloud computing server. Computing devices running the underlying application and/or the data sharing sub-application may communicate with the cloud services via HTTP communication. In some implementations, communications from computing devices pass through a network firewall and/or a load balancer prior to arriving at the cloud computing system. The cloud computing system may include one or more databases. The database(s) may communicate with a push notification manager. The push notification manager may be part of the cloud computing system or may be separate from the cloud computing system. The push notification manager may communicate with a push notification service provider. Communication between the push notification manager and the push notification service provider may be via HTTP communication. The push notification service provider, in some implementations, communicates with a push notification management system. The push notification management system may be specific to the computing device. In some implementations, the push notification management system communicates with the computing device to provide push notifications. The push notification management system, in some implementations, communicates via Raw TCP with the computing device to provide push notifications.

Figure 7:
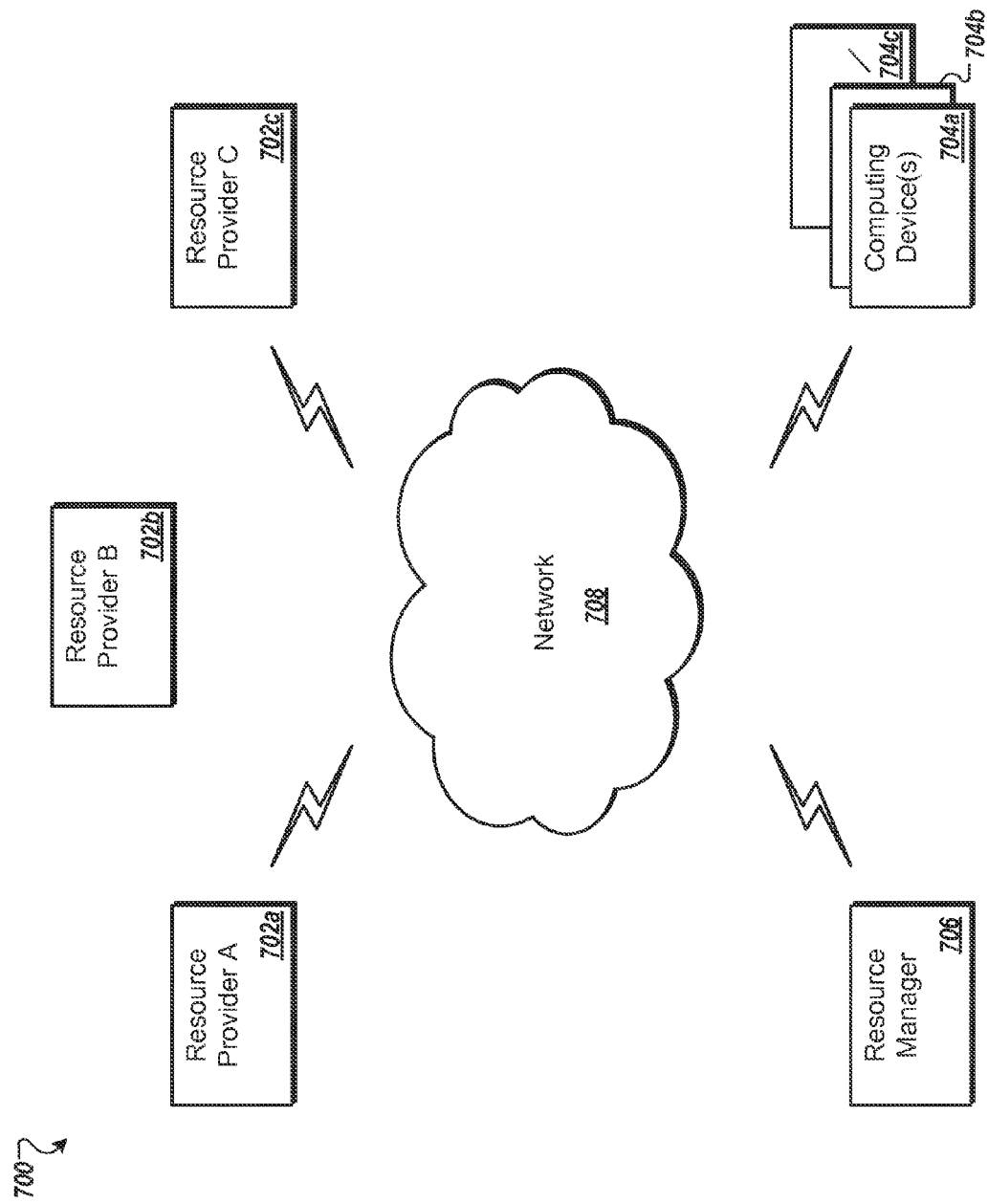
FIG. 7 is a block diagram of an example network environment.

As shown in FIG. 7, an implementation of an exemplary cloud computing environment 700 for gesture-based sharing of data between separate computing devices is shown and described. In brief overview, the cloud computing environment 700 may include one or more resource providers 702a, 702b, 702c (collectively, 702). Each resource provider 702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 702 may be connected to any other resource provider 702 in the cloud computing environment 700. In some implementations, the resource providers 702 may be connected over a computer network 708. Each resource provider 702 may be connected to one or more computing device 704a, 704b, 704c (collectively, 704), over the computer network 708.

The cloud computing environment 700 may include a resource manager 706. The resource manager 706 may be connected to the resource providers 702 and the computing devices 704 over the computer network 708. In some implementations, the resource manager 706 may facilitate the provision of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 may establish a connection between a particular resource provider 702 and a particular computing device 704. In some implementations, the resource manager 706 may redirect a particular computing device 704 to a particular resource provider 702 with the requested computing resource.

Figure 8:
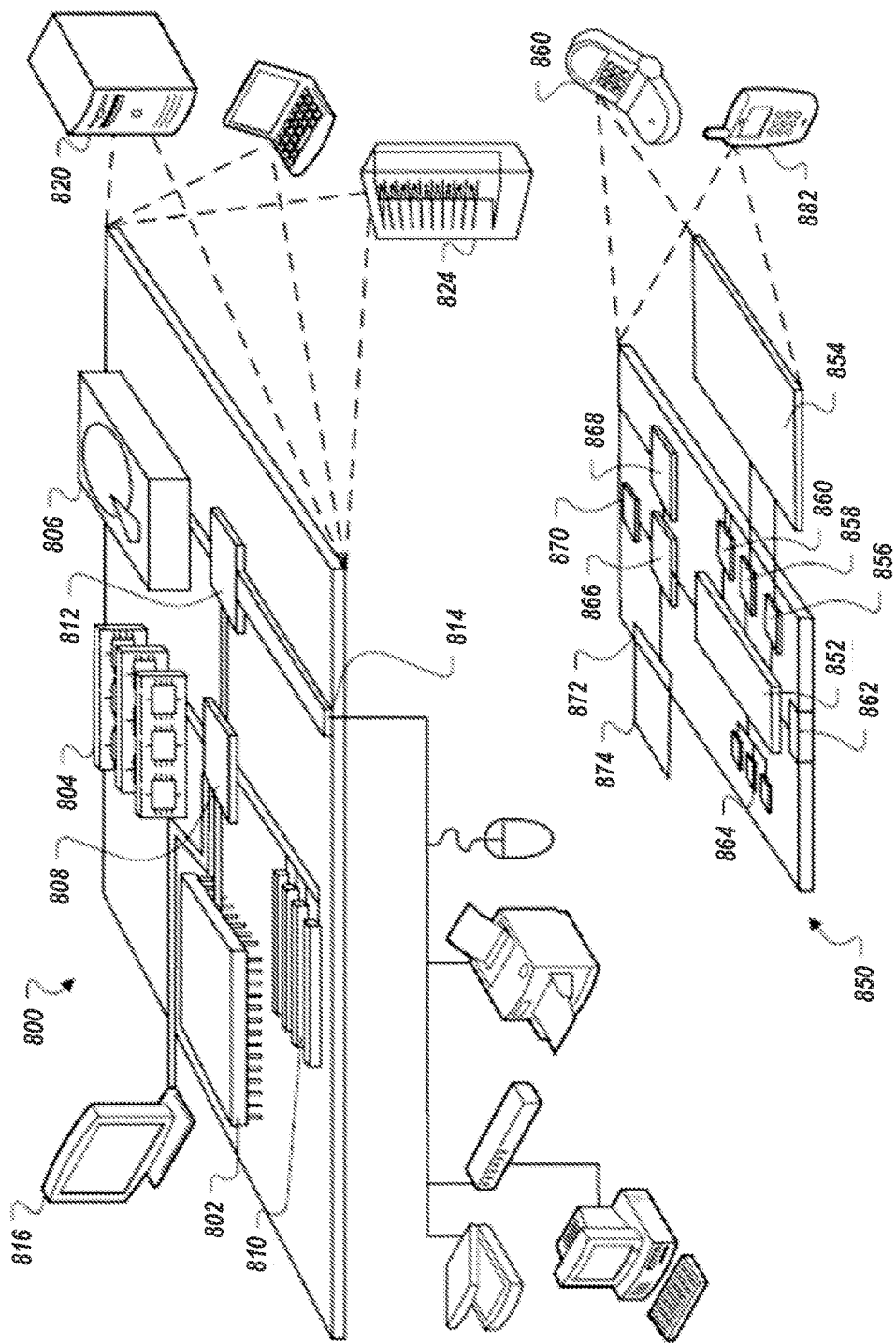
FIG. 8 is a block diagram of an example computing device and an example mobile computing device.

FIG. 8 shows an example of a computing device 800 and a mobile computing device 850 that can be used to implement the techniques described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, computerized eye glasses, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provide as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 852), perform one or more methods, such as those described above. The instructions can also be stored by one or more storage devices, such as one or more computer- or machine-readable mediums (for example, the memory 864, the expansion memory 874, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

It should also be noted that embodiments of the present disclosure may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA™. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

In view of the structure, functions and apparatus of the systems and methods described here, in some implementations, systems, methods, and apparatus for gesture-based sharing of data between two or more computing devices are provided. Having described certain implementations of methods and apparatus for gesture-based sharing of data between two or more computing devices, it will now become apparent to one of skill in the art that other implementations incorporating the concepts of the disclosure may be used. Therefore, the disclosure should not be limited to certain implementations, but rather should be limited only by the spirit and scope of the following claims.

The invention claimed is:

1. A method of sharing files via a network-based sharing service, the method comprising:
   receiving, via a network, from a first data share application executing on a first user computing device, a request to identify members available for sharing;
   identifying, by a processor of a computing device, one or more members available for sharing, wherein each of the one or more members available for sharing is associated with a respective member computing device executing a data share application in communication with the network-based sharing service;
   for each member of at least a portion of the one or more members identified as available for sharing:
      receiving, via the network, from the data share application executing on the respective member computing device, a list of eligible file types associated with one or more applications installed on the respective member computing device; and
      providing, via the network, to the first data share application, the list of eligible file types;
   receiving, via the network from the first data share application, a request for data share, wherein the request comprises at least one file and a member identifier associated with a target user of the one or more members available for sharing;
   determining, by the processor, an identification of a second user computing device, wherein
      the member identifier associated with the target user is matched to account information stored in a member device database of the network-based sharing service, and
      the second user computing device is associated with a computing device identifier stored in the member device database and associated with the account information matched to the member identifier associated with the target user;
   issuing, by the processor, via the network, an alert to the target user regarding data availability, wherein the alert is issued through a second data share application installed on the second user computing device;
   responsive to the alert, receiving, from the second user computing device, a request for available data; and
   responsive to the request for available data,
      retrieving, by the processor, the at least one file, and
      providing, via the network, the at least one file, wherein the at least one file is provided to the second data share application.

2. The method of claim 1, wherein
   the first data share application comprises a sub-application in communication with a software application; and
   identifying the one or more members available for sharing comprises identifying respective ability of each computing device associated with the one or more member identifiers to view a file type associated with the software application.

3. A system for sharing files via a network-based sharing service, the system comprising:
   a processor; and
   a memory having instructions stored thereon, wherein the instructions, when executed by the processor, cause the processor to:
      receive, via a network, from a first data share application executing on a first user computing device, a request to identify members available for sharing;
      identify one or more members available for sharing, wherein each of the one or more members available for sharing is associated with a respective member computing device executing a data share application in communication with the network-based sharing service;
      for each member of at least a portion of the one or more members available for sharing:
         receive, via the network, from the data share application executing on the respective member computing device, a list of eligible file types associated with one or more applications installed on the respective member computing device; and
         provide, via the network, to the first data share application, the list of eligible file types;
      receive, via the network from the first data share application installed on a first user computing device, a request for data share, wherein the request comprises at least one file and at least one member identifier associated with at least one target user of the one or more members available for sharing;
      determine an identification of a second user computing device, wherein the second user computing device wherein
         a first member identifier is matched to account information stored in a member device database of the network-based sharing service, and
         the second user computing device is associated with a computing device identifier stored in the member device database and associated with the account information matched to the first member identifier;
      issue, via the network, an alert to the target user regarding data availability, wherein the alert is issued through a second data share application installed on the second user computing device;
      responsive to the alert, receive, from the second user computing device, a request for available data; and
      responsive to the request for available data,
         retrieve the at least one file, and
         provide, via the network, the at least one file, wherein the at least one file is provided to the second data share application.

* * * * *